United States Patent [19]

Benson et al.

[11] Patent Number: 5,202,264

[45] Date of Patent: * Apr. 13, 1993

[54] ELISA USING MULTI-SPECIES ANTIBODIES FOR DETECTION OF VON WILLEBRAND FACTOR IN MULTIPLE SPECIES

[75] Inventors: Roger E. Benson, Albany; James L. Catalfamo, South Bethlehem, both of N.Y.; W. Jean Dodds, Santa Monica, Calif.

[73] Assignee: Health Research, Incorporated, Albany, N.Y.

[*] Notice: The portion of the term of this patent subsequent to Mar. 23, 2010 has been disclaimed.

[21] Appl. No.: 604,885

[22] Filed: Oct. 26, 1990

Related U.S. Application Data

[63] Continuation-in-part of Ser. No. 428,161, Jan. 11, 1990.

[51] Int. Cl.$^5$ ................. G01N 33/53; G01N 33/543; C07K 15/02; C07K 15/28
[52] U.S. Cl. ................ 435/7.94; 435/7.1; 436/518; 530/383; 530/388.25; 530/387.1
[58] Field of Search ............. 436/518; 435/7.1, 7.94; 530/383, 388.25, 387.1

[56] References Cited

U.S. PATENT DOCUMENTS

| | | | |
|---|---|---|---|
| 4,376,110 | 3/1983 | David et al. | 436/513 |
| 4,486,530 | 12/1984 | David et al. | 435/7 |
| 4,578,218 | 3/1986 | Saundry et al. | 530/383 |
| 4,666,865 | 5/1987 | Chang et al. | 436/518 |
| 4,687,747 | 8/1987 | Lin | 436/518 |
| 4,748,110 | 5/1988 | Paul | 435/5 |

OTHER PUBLICATIONS

Benjamin et al., "A Unique Epitope on Human Serum Albumin recognized by Monoclonal Antibody HSA-1: A Probe for Identification of the Human Origin of Blood or Tissue," Hybridoma 6, 183-190 (1987).
Silveira, A. M. V., et al., Thrombosis Research 43: 91-102 (1986).
Taylor, L. D., Thrombosis and Haemostasis 59: 251-254 (1988).
Wang, H. X., et al., J. Clin Pathol 38: 317-319 (1985).
Yamamoto, T., et al., Thrombosis Resesarch 45: 59-74 (1987).
Yorde, L. D., et al., Clin. Chem. 25: 1924-1927 (1979).
Zimmerman, T. S., et al., J. Lab. Clin. Med. 86: 152-159 (1975).
Zimmerman, T. S., et al., J. Clin. Investigation 50: 244-254 (1971).
Bennett, B. and Ratnoff, W. D., Proc Soc Exp Biol Med 143: 701-706 (1973).
Benson, R. E. & Dodds, W. J., Br J Haematol 31: 437-446 (1975).
Bouma, B. N., et al., Scand J Haematol 17: 263-275 (1976).
Clowes, A. W., et al., Lab Invest 39: 141-149 (1978).
Coppola, R., et al., Thrombosis Research 17: 473-480 (1980).
Cotter, S. M., et al., J Am Vet Med Assoc 172: 166-168 (1978).
Griggs, T. R., et al., Proc Natl Acad Sci USA 74: 759-763 (1977).
Johnson, G. S., et al., Thrombosis Research 42: 419-423 (1986).
Meyer, D., et al., Br J Haematol 57: 597-608 (1984).
Nachman, R., et al., J Clin Invest 60: 914-920 (1977).

(List continued on next page.)

Primary Examiner—Christine M. Nucker
Assistant Examiner—M. P. Woodward
Attorney, Agent, or Firm—Heslin & Rothenberg

[57] ABSTRACT

The subject invention provides an antibody directed to von Willebrand factor antigen characterized by being capable of recognizing an epitope of the von Willebrand factor antigen, the epitope being evolutionarily conserved among vertebrate species. The subject invention further provides a method for the qualitative and quantitative detection of von Willebrand factor in multiple species using an enzyme-linked immunosorbent assay and the antibodies of the subject invention.

82 Claims, 12 Drawing Sheets

OTHER PUBLICATIONS

Olson, J. D., et al., J Lab Clin Med 89: 1278–1293 (1977).
Schmer, G., et al., J Biol Chem 247: 2512–2521 (1972).
Turitto, V. T., et al., Blood 65: 823–831 (1985).
Verweij, C., et al., EMBO J. 5: 1839–1847 (1986).
Pietu, G., et al., Biochem Biophys Res Comm 163: 618–626 (1989).
Bahou, W., et al., J Clin Invest 84: 56–61 (1989).
Brinkhous, K., et al., Embase Abstract No. 86008826 of Semin Thromb Hemost 11: 337–341 (1985).
Chand, S., et al., Embase Abstract No. 86198216 of Throm Haemostasis 55: 318–324 (1986).
Thorsen, L., et al., Embase Abstract No. 84035971 of Throm Haemostasis 57: 212–216 (1987).
Silverman, C., et al., J Lab Clin Med 110: 113–118 (1987).
Bowie, E. J. W., et al., Blood 62: 146–151 (1983).
Bradley, L. A., et al., Clin. Chem. 30: 87–92 (1984).
Brien, W. F., & Stewart, M. W., Clin. Biochemistry 19:179–182 (1986).
Brown, J. E., & Bosak, J. O., Thrombosis Research 43:303–311 (1986).
Casanato, A., & Girolami, A., Folia Haematol. 113: 670–684 (1986).
Cejka, J., Clin. Chem. 28: 1356–1358 (1982).
Fishman, D. J., et al., Blood 59: 1163–1168 (1982).
Furlong, R. A., et al., Clin. lab. Haemat. 10: 295–305 (1988).
Handin, R. I., & Wagner, D. D., Progress in Hemostasis and Thrombosis 9: 233–259 (1989).
Ingerslev, J., Scand J Clin Lab Invest 47: 143–149 (1987).
Ingerslev, J., et al., Clinica Chimica Acta 174: 65–82 (1988).
Inoue, K., et al., Chem. Pharm. Bull. 34: 2550–2554 (1986).
Katzmann, J. A., et al., Blood 58: 530–536 (1981).
Mascelli, M. A., et al., Biochemistry 25: 6325–6335 (1986).
Mascelli, M. A., & Kirby, E. P., Biochemistry 27: 1274–1284 (1988).
Meyers, K. M., et al., Thrombosis Research 57: 109–116 (1990).
Ness, P. M., & Perkins, H. A., Thrombosis. Haemostas. 42:848–853 (1979).
Ogata, K., et al., Blood 61: 27–35 (1983).
Peake, I. R., & Bloom, A. L., Thrombosis Research 10: 27–32 (1977).
Rodeghiero, F., et al., Blood 69: 454–459 (1987).
Short, P. E., et al., Medical Lab. Sciences 39: 351–355 (1982).
Ardaillou, N., et al., Thrombosis Research 12: 817–830 (1978).
Bartlett, A., et al., Br Med J 1: 994–996 (1976).
Benson, R. E., et al., Thrombosis Research 7: 383–389 (1975).
Benson, R. E., et al., Amer. J. Vet. Research 44: 399–403 (1983).
Benson, R. E., et al., Vet. Immunology & Immunopath. 7:337–346 (1984).
Benson, R. E., & Dodds, W. J., Vet. Immun. & Immunopath 11:21–30 (1986).

Absorbance at 490nm in each vWf fraction

ELISA USING MULTI-SPECIES ANTIBODIES FOR DETECTION OF VON WILLEBRAND FACTOR IN MULTIPLE SPECIES

This invention was made with partial support under Grant No. HL09902 from the National Institutes of Heath, U.S. Department of Health and Human Services. Accordingly, the U.S. Government has certain rights in the invention.

This application is a continuation-in-part of U.S. Ser. No. 428,161 filed Jan. 11, 1990, the contents of which are hereby incorporated by reference into this application.

FIELD OF THE INVENTION

The subject invention is directed to the qualitative and quantitative detection of von Willebrand factor (vWf) in multiple vertebrate species using an enzyme-linked immunosorbent assay (ELISA). The assay utilizes antibodies from multiple species capable of recognizing an epitope of von Willebrand factor antigen which is evolutionarily conserved among vertebrate species.

BACKGROUND OF THE INVENTION

Throughout this application various publications are referenced by arabic numerals within parentheses. Full citations for these references may be found at the end of the specification immediately preceding the claims. The disclosures of these publications in their entireties are hereby incorporated by reference in this application in order to more fully describe the state of the art to which the invention pertains.

Factor VIII/vWf is a plasma coagulation complex composed of two differently sized, noncovalently linked, and genetically independent proteins. The higher molecular weight component that is involved in platelet-vessel wall interactions is termed von Willebrand factor (vWf). vWf is a multimeric glycoprotein which plays an essential role in the hemostatic process. It is deficient and/or defective in the inherited bleeding disorder von Willebrands disease (vWd). The lower molecular weight component, factor VIII-coagulant (VIII:C), is deficient and/or defective in the inherited disorder, hemophilia A. Many acquired disease states can also exhibit low levels of vWf and VIII:C. In contrast, elevated levels of vWf and VIII:C are associated with acute and chronic inflammatory diseases, cancers and thrombotic states.

The laboratory diagnosis of vWd is dependent on demonstrating decreased levels of plasma vWf. Measurement of plasma von Willebrand factor by electroimmunoassay (EIA) or radioimmunoassay (RIA) is currently an important clinical diagnostic and research tool to determine whether an individual is affected with von Willebrand's disease (vWd), one of the most common bleeding disorders of man and domestic animals. Recent estimates of the gene frequency of inherited, congenital vWd in humans range from 1 to 500 to as high as one in 50 live births of either sex, whereas in inbred purebred dog families, prevalence can be as high as 80% (Doberman pinschers) and varies between 15 to 45% in many other breeds. Furthermore, an acquired form of vWd is increasingly being recognized in association with autoimmune thyroiditis in humans and dogs.

In addition to the vWf deficiency states that lead to a clinically expressed bleeding tendency, vWf is known to be an important contributor to the development or promotion of cardiovascular disease. Monitoring vWf levels is thus valuable in both clinical and experimental assessment of thrombosis and atherogenesis, for example, in patients and for long-term cardiovascular and aging studies in captive primates.

Thus, as physicians and veterinary clinicians have become increasingly aware of the prevalence of vWd as a cause of or precipitating factor in bleeding, the demand for a practical and inexpensive screening test for vWF has arisen. Currently the EIA or RIA procedures utilized routinely require expensive equipment, potentially toxic reagents, sophisticated technology, and skilled technologists. These tests are labor-intensive assays which increase the actual and retail cost of the assay.

There is a need within the field for a sensitive assay which is quantitative, specific, easy to perform and has increased efficiency. Such an assay would be especially advantageous to the Veterinary Hematology Laboratory of the State of New York Department of Health, which routinely analyses vWf antigen levels by EIA of more than 10,000 samples per year of humans, dogs and other species.

In order to permit the measurement of trace amounts of platelet vWf for research purposes, and to improve the sensitivity of routine electroimmunoassay for plasma vWf, the subject invention provides a qualitative and quantitative, highly sensitive, specific, and reproducible enzyme-linked immunosorbent assay (ELISA) for vWf.

The ELISA of the subject invention utilizes antibodies from multiple species which can be used to detect von Willebrand factor antigen in multiple species.

Previous ELISAs that measure human vWf have been described in the literature. A significant disadvantage, however, of these procedures is the necessary rabbit and goat antibodies to vWf are raised against human vWf. Because the original source of material for preparing the immunogen is human plasma, it presents the danger of transmitting blood-borne diseases to other humans. The subject invention provides an assay which does not depend upon the utilization of vWf man plasma from human plasma to raise antibodies and, therefore, has little infectious potential.

In addition to humans and dogs, the assay of the subject invention can quantitatively determine vWf levels in many other domestic and laboratory animal species including but not limited to non-human primates, horse, pig, mouse, rat, guinea pig, cow and cat. Previously, accurate measurements of vWf were not possible for many of these species. Utilizing the ELISA assay of the subject invention applicants have diagnosed vWd for the first time in a valuable quarterhorse with a significant bleeding history. The subject assay can thus be used to screen valuable racing and working horse stock for the presence of vWd. For example, exercise-induced pulmonary hemorrhage in horses is a relatively common and serious problem of complex etiology that remains poorly understood.

The ELISA assay of the subject invention solves a long standing problem which has not been recognized by those working in the area of human von Willebrand factor. This long standing problem, however, has become apparent to applicants as researchers in the area of von Willebrand factor in connection with numerous species. The problem relates to the need for an assay which can be used to qualitatively and quantitatively detect von Willebrand factor antigen in multiple species without the need to create or purchase an assay which is specific for each individual species, for example, rat, guinea pig, mice, etc. It is impractical in the research area to have individual vWf assays for each species which may be encountered in the course of research relating to vWf. Thus, the diagnostic kits of the subject invention unexpectedly solve this long standing problem which has previously been unrecognized in the vWf field. This assay will be of particular use in research work where investigators can evaluate von Willebrand factor with a fast and efficient assay useful for each of these species. Furthermore, the ELISA assay of the subject invention is much more sensitive than previous EIA or RIA assays for vWf, and thus provides a definite advantage over the previously used conventional assays.

Research into developing assays for von Willebrand factor in the past which would quantitate vWf in such diverse multiple species have been unsuccessful, where the assay of the subject invention has succeeded.

Silveira et al. (36) have described a sandwich ELISA system to measure plasma von Willebrand factor antigen (vWf:Ag) in humans. The test utilizes antibodies to human vWf:Ag raised in rabbits. The rabbit antibody is immobilized in the wells of a microtiter plate and acts as the reactive capture surface for vWf:Ag. Serially diluted plasma samples containing either known or unknown levels of vWf:Ag are reacted with the immobilized antibody, and then quantified by detection with a second (sandwich) antibody to human vWf:Ag (goat antihuman vWf:Ag) and a horseradish peroxidase-conjugated porcine anti-goat IgG. The peroxidase activity generated by the final antibody is proportional to the captured amount of vWf:Ag and is measured by the color change it catalyses in the substrate orthophenylenediamine (OPD). The color change reaction is subsequently quenched with sulfuric acid and the optical density measured to determine the concentration of vWf:Ag in the plasma tested.

A disadvantage of the above process is that the rabbit and goat antibodies to vWf which function as the initial capture, immobilizing or anchor antibody and the second or sandwich antibody are raised against human vWf:Ag. Because the original source material for preparing human vWf:Ag is human blood, it presents the danger of transmitting blood-borne diseases to other humans. As a result, the test should only be employed in specially equipped and sanitized laboratories designated for handling specimens of human origin (37). Furthermore, this ELISA assay is not used to detect vWf:Ag in a wide variety of vertebrate species.

Zimmerman et al. (1) describe an immunoassay to quantify the plasma protein deficient in human vWd by utilizing a precipitating antibody prepared in rabbits. This development initiated a series of studies that led to a substantial increase in the understanding of the structure and function of the factor VIII - von Willebrand factor complex (2-4). Parallel studies conducted with animal models of hemophilia A and vWd led to similar findings (5-8). The measurement and identification of vWf:Ag in the plasma and cells of these animals required preparation of polyclonal antisera specific for the vWf:Ag of each species. The development of species-specific antibodies in rabbits and goats against dog (9,10), pig (7,11), rat (12), guinea pig (13), cow (14), and rabbit vWf:Ag (15,16) has been reported. As in Silveira et al., this assay is not used to detect vWf:Ag in a wide variety of vertebrate as is the assay of the subject invention.

Bennett and Ratnoff (17) reported precipitin reactions of partial identity between rabbit antihuman vWf:Ag and the plasmas of 15 different mammalian species, while Coppola et al. (18) demonstrated cross-reactivity of four nonhuman primate plasmas and 20 other mammalian plasmas in a two-site immunoradiometric assay using either human homologous or rabbit heterologous antibodies. Bouma et al. (19) published the first quantitative cross-species data whereby canine vWf:Ag was determined with rabbit antibodies specific for human vWf:Ag. It was subsequently found that species cross-reactivity permitted the measurement of feline (20) and equine vWf:Ag (21) with the anti-canine vWf:Ag reagent. Again, the diverse vertebrate species in which the subject assay can be used to measure vWf:Ag are not disclosed by these references, and thus do not provide the advantages, i.e. to researchers, which the subject assay provides.

Utilizing monoclonal antibodies, it has been demonstrated that cross-reactivity exists between antibodies to porcine (22) or bovine (23) vWf:Ag and human vWf:Ag, and between antihuman vWf:Ag and canine (24), porcine and bovine vWf:Ag (24,25).

Katzman et. al. (22) describe twenty monoclonal antibodies developed against porcine vWf antigen and indicate that six of these clones were also active against human vWf antigen. These antibodies were not used in a quantitative fashion, ELISA or otherwise, to measure human vWf antigen and information on other species cross-reactivity was not disclosed.

Bradley, Franco and Reisner (23) disclose two monoclonal antibodies to human vWf antigen which could be used to quantify vWf antigen in porcine, bovine and canine samples. No details, however, of the methodology for quantitation of the animal vWf was provided. Their assay used antibodies prepared against human material and therefore maintained the potential for infectious transmission. The safety feature of antibodies to non-human products, therefore, remains a benefit of the subject invention. An additional difference between a preferred embodiment of the subject invention and the assay of the Bradley et al. reference is that the technique in the reference is competitive and does not utilize a capture antibody.

As with polyclonal antibodies, none of these assays utilizing monoclonal antibodies disclose the diverse vertebrate species for which the assay of the subject invention can be used.

Peake and Bloom (38) disclose an immunoradiometric assay for von Willebrands factor which was not cross-species reactive.

Prior to the subject invention, most of the assays for von Willebrand factor discussed in the literature have been applied to humans successfully. However, when they are used to look at multiple species, they are not successful. This may be due to the fact that the assays are not of the proper configuration or the antibodies used do not recognize conserved epitopes.

Cross-species reactivity between humans and dogs is well known to experts in the field. For example, it has been published that anti-human vWf can be used to quantitate canine vWf by electroimmunoassay. However, qualitative cross-species reactivity between humans and at least 25 or 30 vertebrate species is not known and is not expected because classical assays to measure vWf, for example, the standard Laurell assay, have failed to allow the detection of vWf in these other multiple vertebrate species. This standard Laurell assay allows the measurement using anti-human vWf of dog, cat, monkey and primate vWf antigen. However, it does not allow the detection of horse, rat, guinea pig, pig, cow, rabbit, llama, camel, and manatee, for example.

Applicants have recognized that the problems in regard to recognizing vWf in multiple species are related to three things:

1. The antibody must be capable of reacting with conserved epitopes of the vWf antigen.
2. The antibody must be present in the right configuration in the assay. In other words, the assay must allow the antibody to recognize these conserved epitopes. If the antibody is not present in the right configuration, even if it is capable of recognizing the conserved epitope, it will not do so.
3. There is an advantage to using plasma instead of serum. The reactive epitopes of vWf are sometimes destroyed when serum is made. In humans, serum or plasma will work. However, in other species plasma is required to preserve reactive epitopes.

Applicants have provided a solution to these problems with the subject invention, which provides antibodies capable of recognizing the conserved epitopes, and an assay configuration which allows the antibodies to recognize the epitopes. The diverse number of vertebrate species for which the subject invention can be used to detect vWf:Ag provides a further definite advantage over previous methods for detecting vWf:Ag.

SUMMARY OF THE INVENTION

It is thus an object of the present invention to provide an ELISA assay which can use antibodies from multiple species for the qualitative and quantitative detection of von Willebrand factor antigen in multiple species. It is a further object of the subject invention to provide such an assay for determining vWf antigen which is easy to perform, efficient, accurate and highly sensitive. The method of the subject invention is particularly useful in screening assays which may be performed in a general laboratory or a clinical setting without the need of expensive equipment or highly trained staff, which are necessary for the sophisticated quantitative assays for vWf which are performed in large biomedical and commercial laboratories. The assay of the subject invention may be performed simply in both human hospital laboratories and veterinary laboratories to demonstrate decreased levels of plasma vWf, thus assisting in the laboratory diagnosis of vWd.

It is a further object of the subject invention to provide a method for determining whether humans or other vertebrates are at risk to bleed during surgery or other stress situations caused by inherited or acquired vWd, or are at risk for genetically transmitting vWd.

It is a further object of the subject invention to measure von Willebrand factor levels in individuals experiencing or at risk to develop thrombotic states, cancers, and acute and chronic inflammatory disorders.

It is a further object of the subject invention to provide an assay which is easy to perform, efficient, accurate and highly sensitive which can be performed to detect vWf antigen in humans, non-human primates, dogs, horses, pigs, mice, rats, guinea pigs, rabbits, cows, cats and other vertebrates. These animals are valuable as pets, food sources, work animals, zoological exhibits, and for research. No procedure has heretofore been described in which the same antibodies have been successfully employed with such a large number of species.

It is still a further object of the subject invention to provide an assay for vWf which does not use human reagents, thus eliminating the danger of transmitting blood-borne diseases to humans from human-based reagents.

In furtherance of these objectives, the subject invention provides an antibody directed to von Willebrand factor antigen characterized by being capable of recognizing an epitope of the von Willebrand factor antigen, the epitope being evolutionarily conserved among vertebrate species. This antibody may be a polyclonal antibody, such as one raised in a vertebrate species and purified by adsorption with plasma substantially free of von Willebrand factor antigen, or the antibody may be a monoclonal antibody.

The subject invention also provides various methods for detecting von Willebrand factor antigen in a sample from a vertebrate species. These methods utilize the antibody of the subject invention in various configurations which allow the antibody to recognize the conserved epitope.

For example, in one preferred assay configuration a sample from the vertebrate species is contacted with an antibody of the subject invention, thus allowing the von Willebrand factor antigen present in the sample to bind to the antibody and form a complex therewith. The complex that is this formed is then contacted with a second antibody of the subject invention, so as to form a second complex which includes the antibody initially contacted with the sample, the vWf:Ag, and the second antibody. The second complex is then contacted with a third antibody which is directed to the second antibody and is labelled with a detectable marker, thus forming a third complex which includes the antibody initially contacted with the sample, the vWf:Ag, the second antibody, and the third antibody. The third antibody is then detected, thus detecting the von Willebrand factor antigen present in the sample.

Where the conserved epitope which is recognized by the antibody of the subject invention is a functional epitope, the lack of or abnormality in this functional epitope can be detected using the assays of the subject invention, thus detecting a dysfunction in the von Willebrand factor of the subject.

The subject invention also provides kits for use in qualitatively and quantitatively detecting von Willebrand factor antigen in a test sample. These kits contain amounts of an antibody of the subject invention, which may or may not be labelled with a detectable marker, and may contain an amount of an antibody which is directed towards one of the antibodies of the subject invention. The kits also contain at least one standard sample having a known von Willebrand factor antigen concentration and a control sample substantially free of von Willebrand factor antigen. Using the quantitative kits, several standard samples of varying vWf:Ag concentration are used. The amount of von Willebrand factor antigen in a test sample can be quantitatively determined by determining the amount of von Willebrand factor antigen in each of the test samples, standard samples and control sample, and then comparing these amounts in order to quantitatively determine the amount of von Willebrand factor antigen in the test sample.

BRIEF DESCRIPTION OF THE FIGURES

These and other objects, features and advantages of the invention will be evident from the following detailed description when read in conjunction with the accompanying drawings in which.

DETAILED DESCRIPTION OF THE INVENTION

Figure 1:
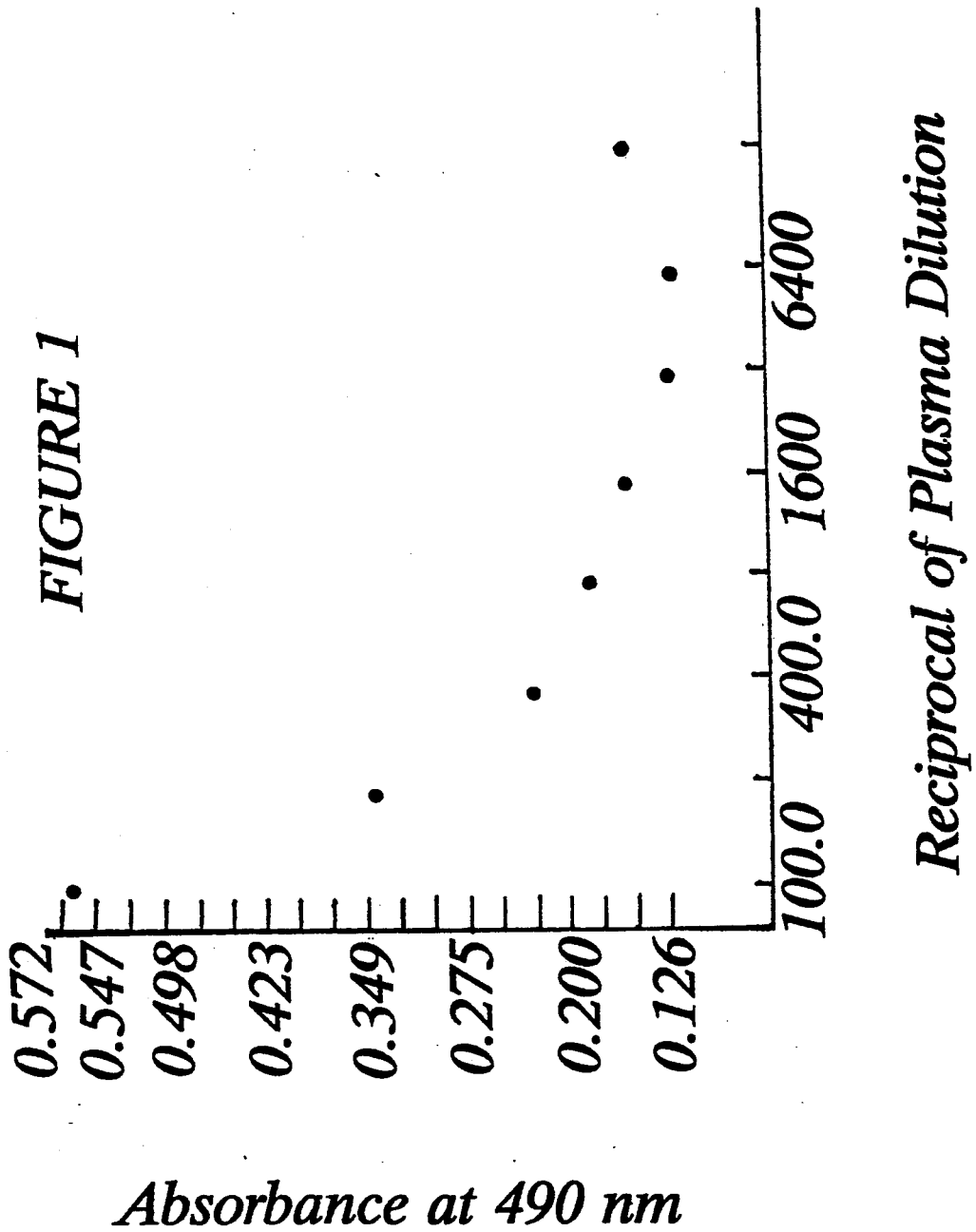
FIG. 1 is a dose response curve for plasma from a cow.
Figure 2:
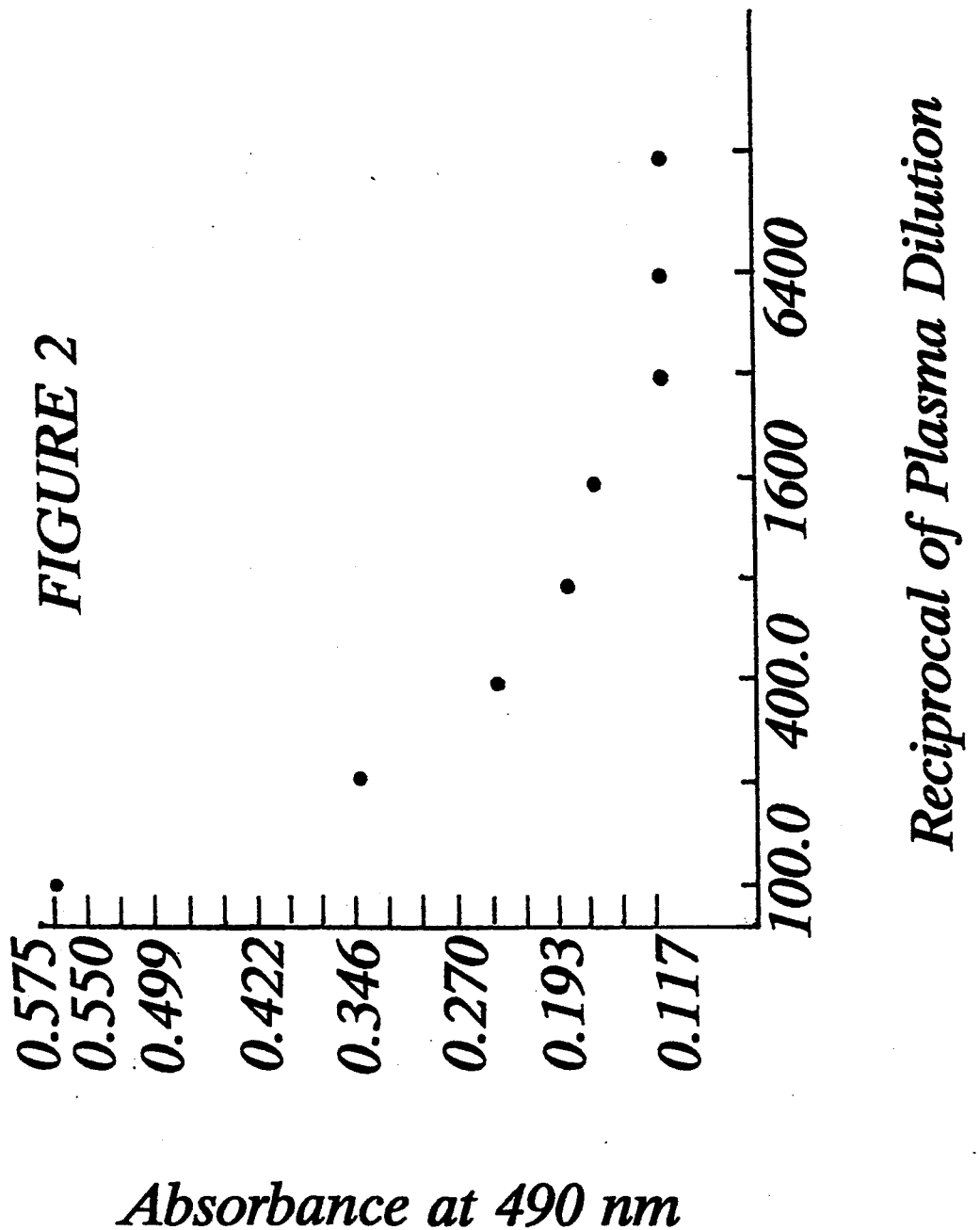
FIG. 2 is a dose response curve for plasma from a sheep.
Figure 3:
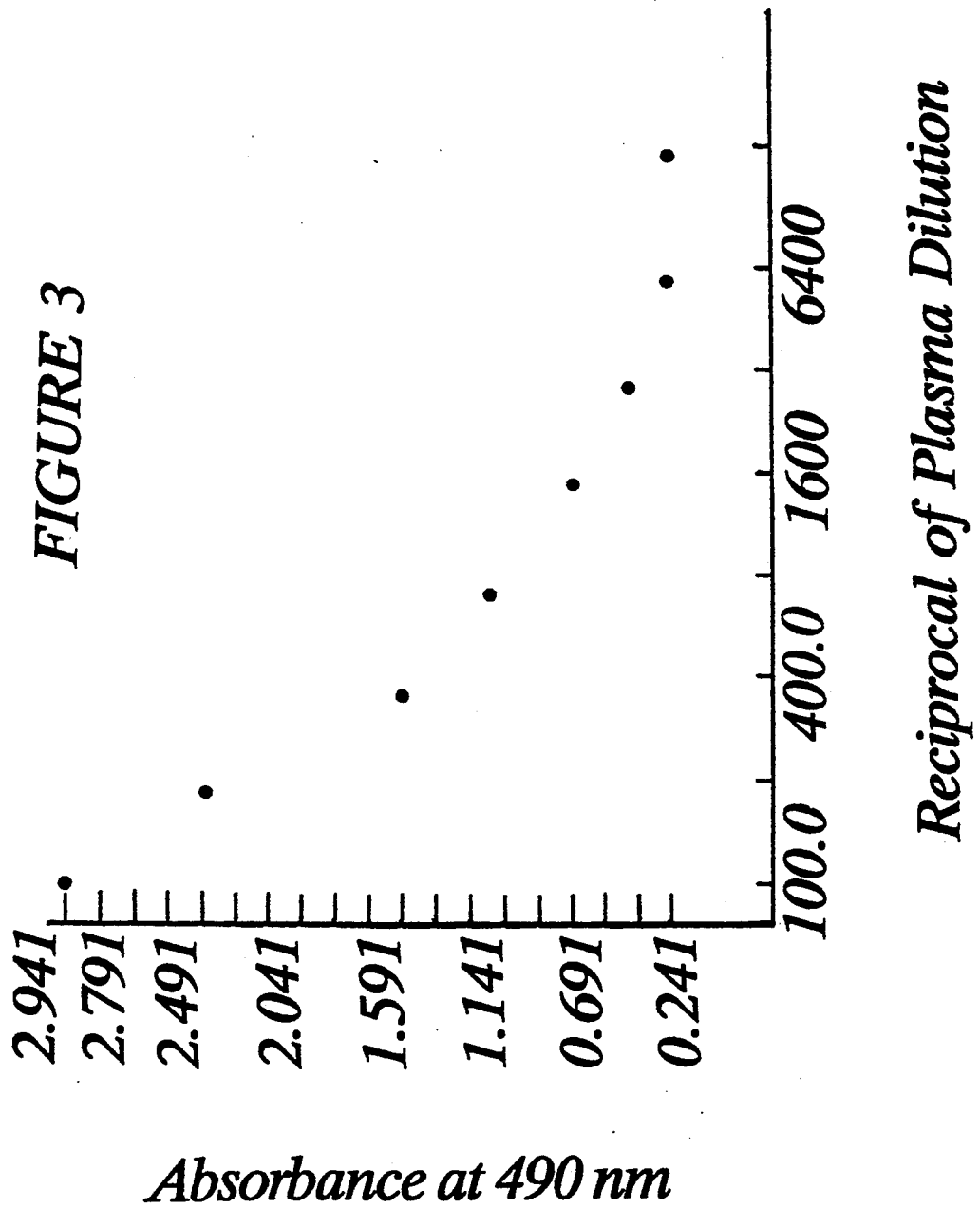
FIG. 3 i a dose response curve for plasma from a monkey.
Figure 4:
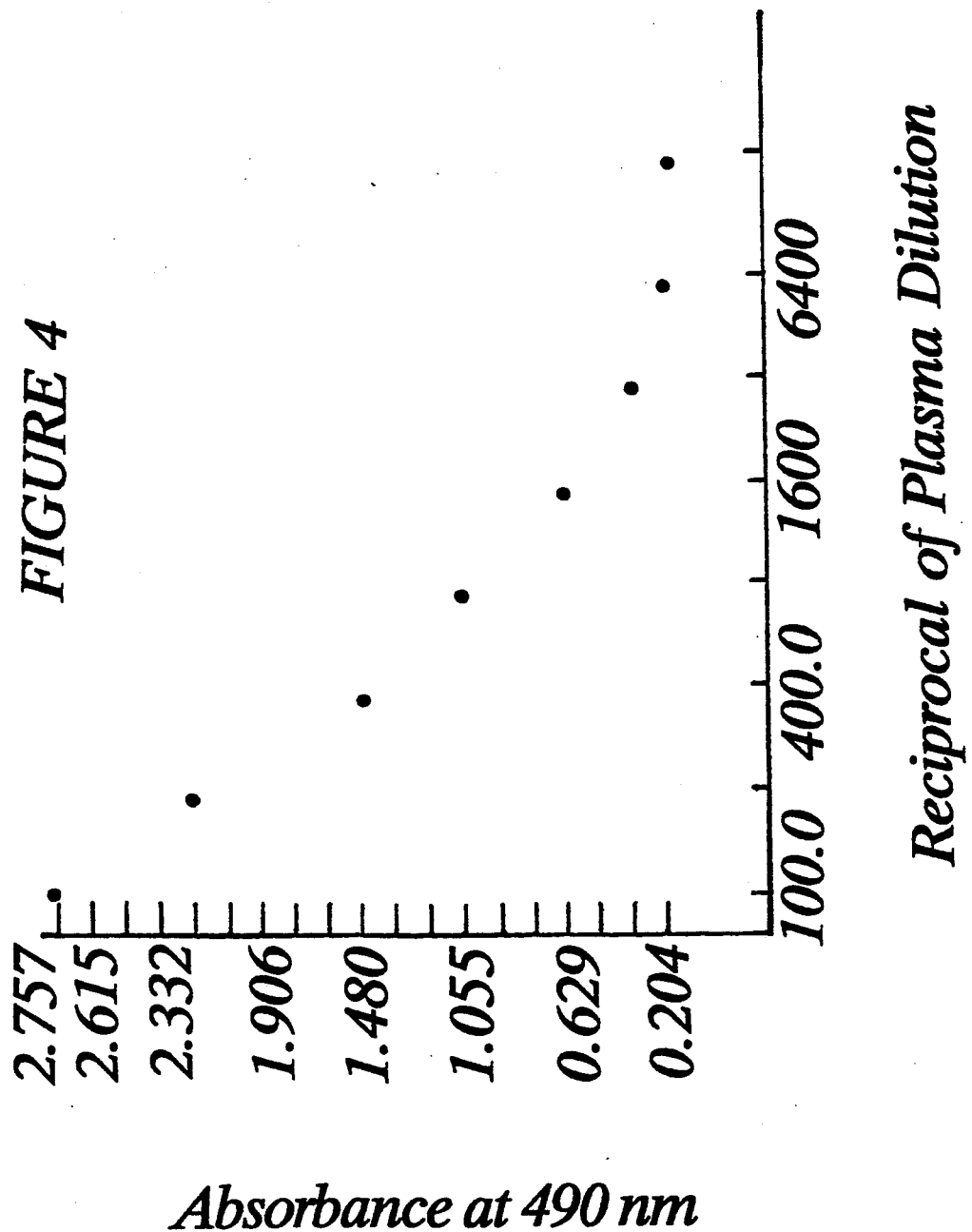
FIG. 4 is a dose response curve for plasma from a cat.
Figure 5:
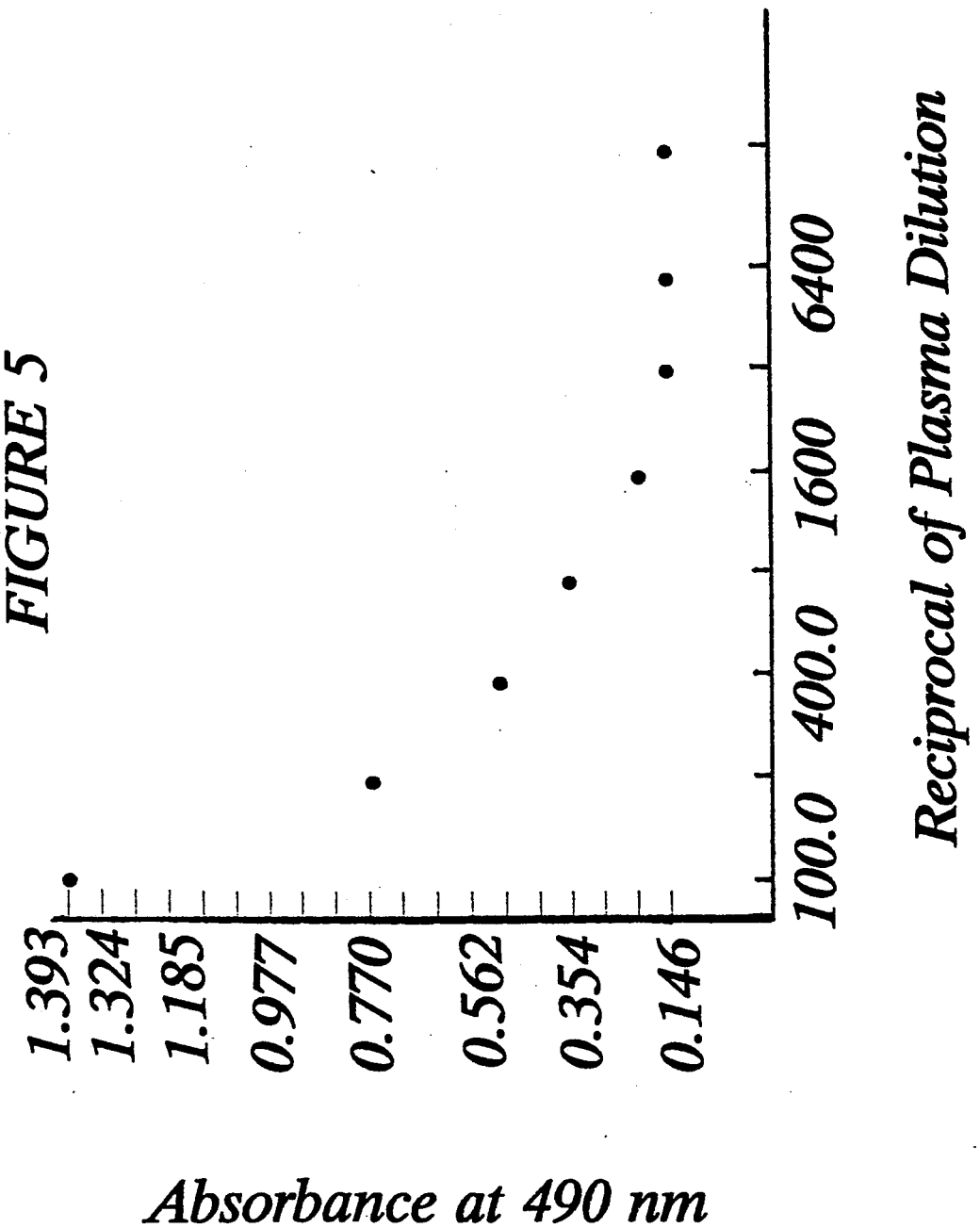
FIG. 5 is a dose response curve for plasma from a rat.
Figure 6:
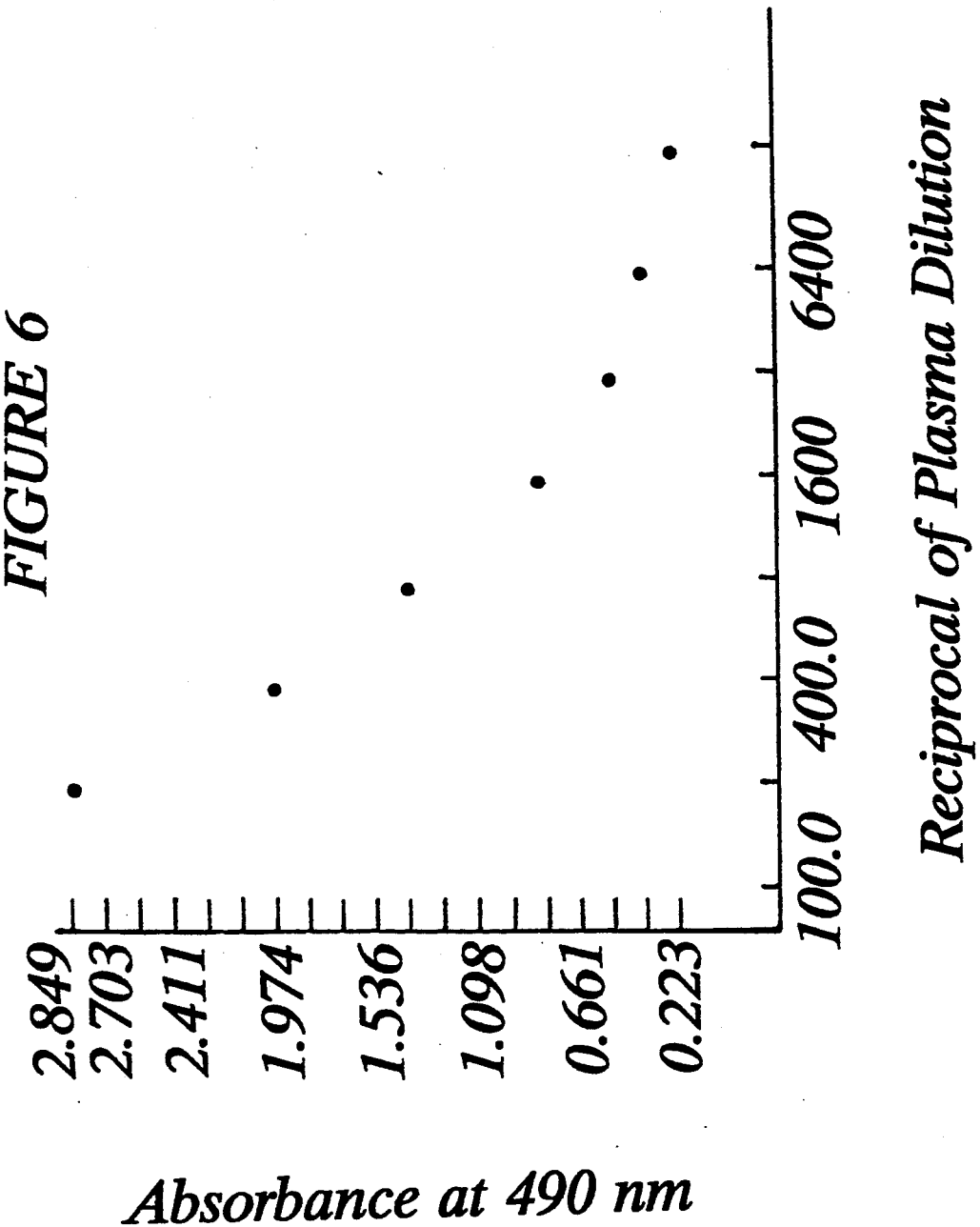
FIG. 6 is a dose response curve for plasma from a dog.
Figure 7:
FIG. 7 is a dose response curve for plasma from a pig.
Figure 8:
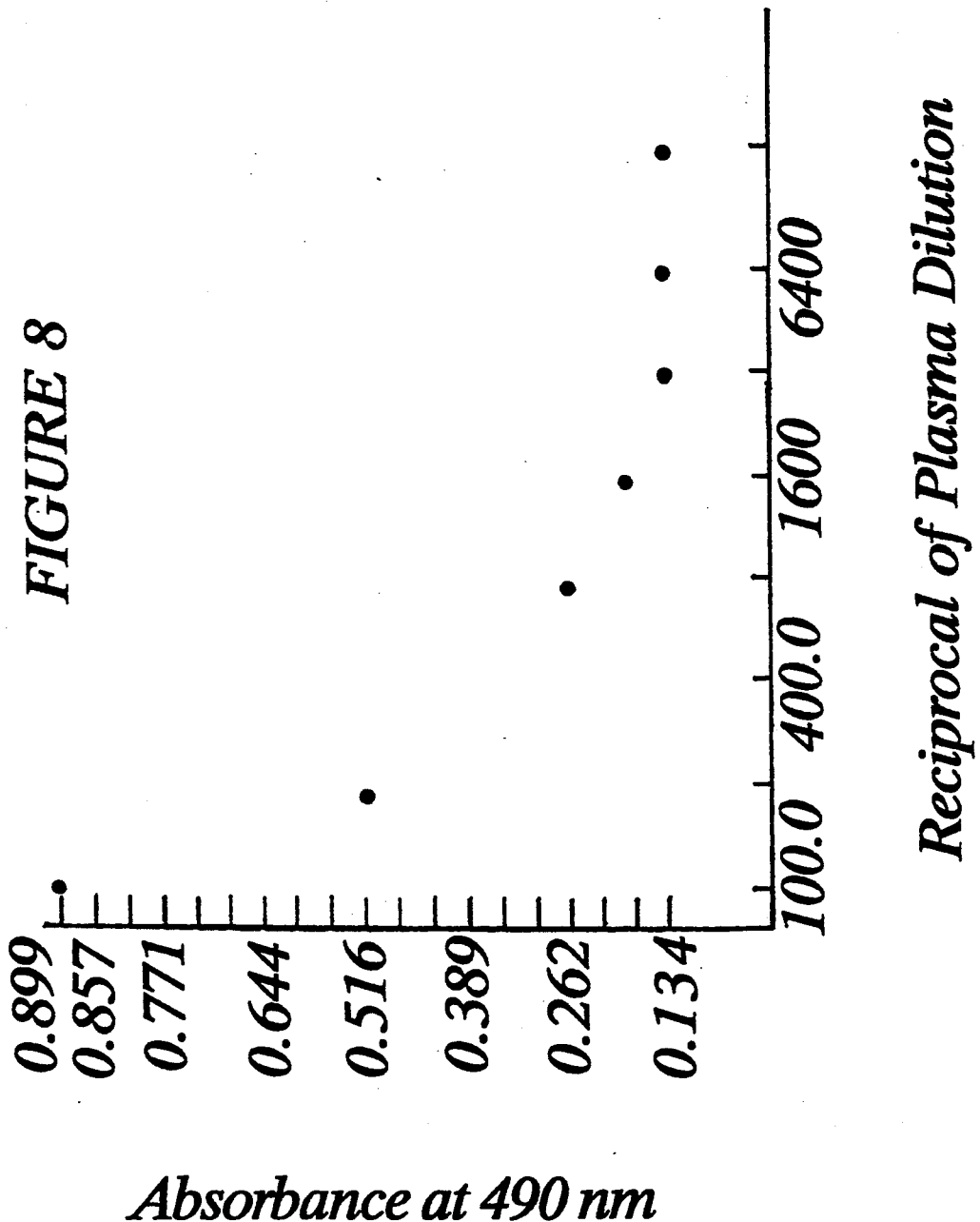
FIG. 8 is a dose response curve for plasma from a goat.
Figure 9:
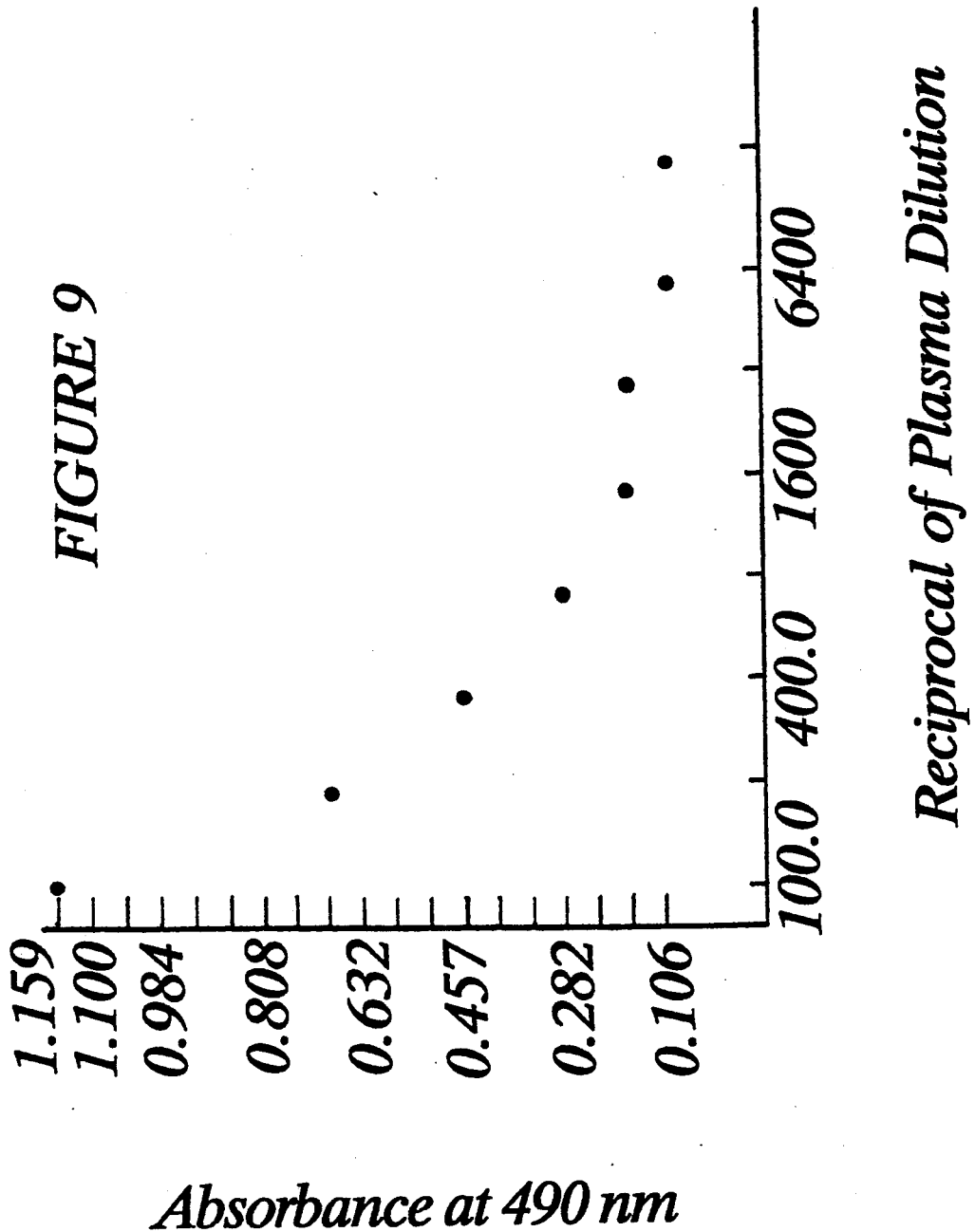
FIG. 9 is a dose response curve for plasma from a mouse.
Figure 10:
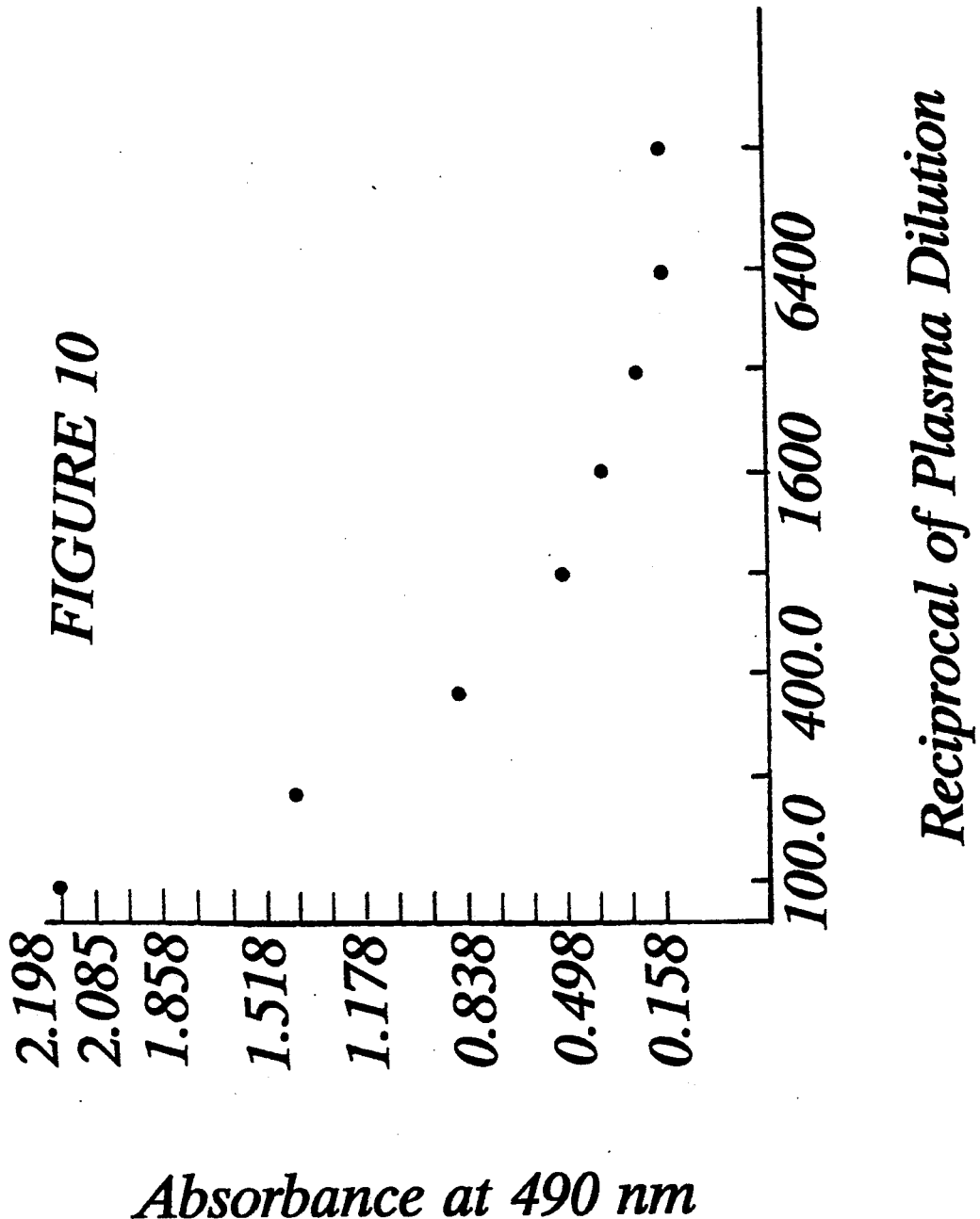
FIG. 10 is a dose response curve for plasma from a horse.
Figure 11:
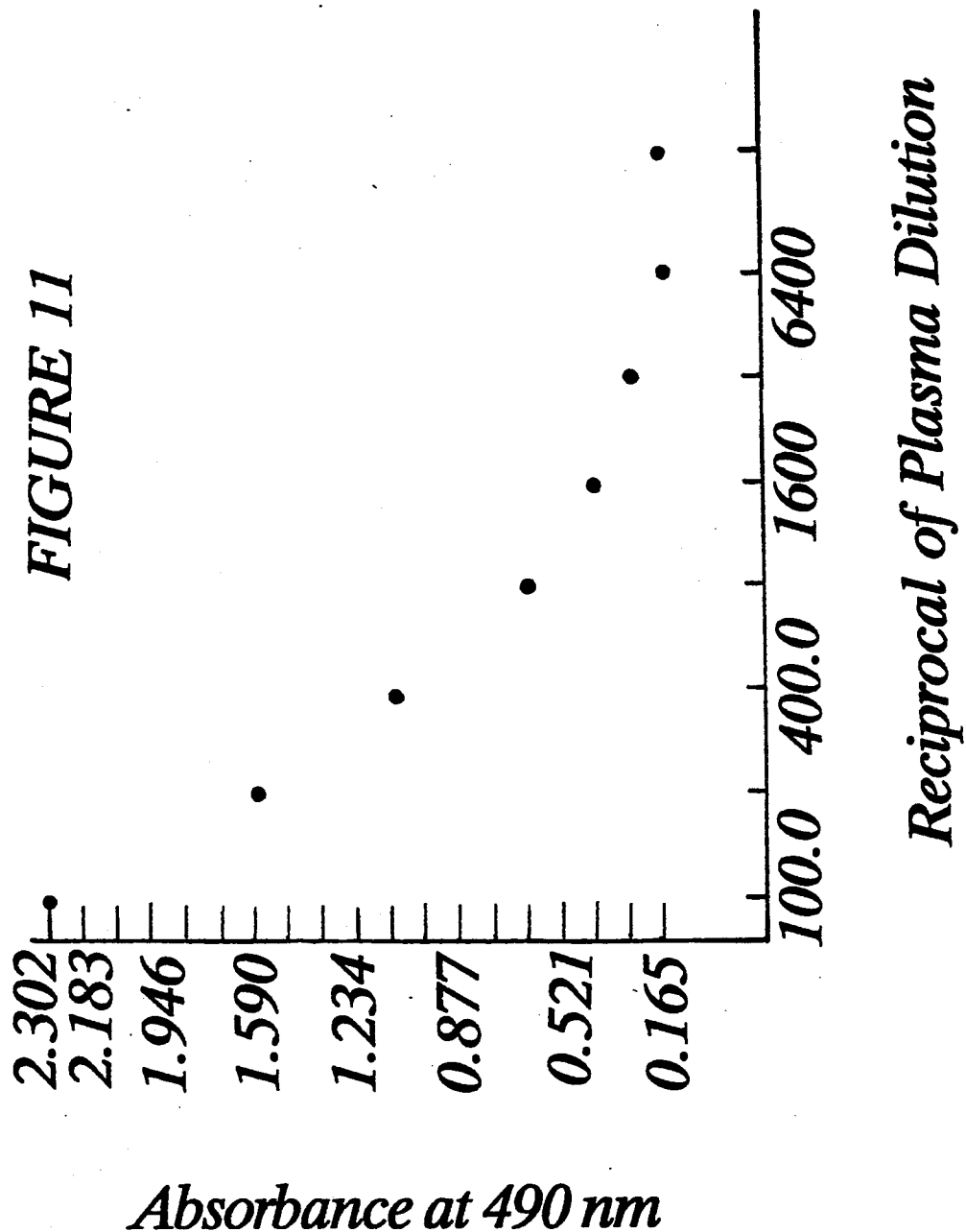
FIG. 11 is a dose response curve for plasma from a guinea pig.

The following abbreviations are used throughout this application:
vWf von Willebrand factor
vWd von Willebrands disease
vWf:Ag von Willebrand factor antigen
ELISA Enzyme Linked Immunosorbent Assay
$V_o$ Void volume
Mab Monoclonal antibody
IgG Immunoglobulin G The subject invention provides an antibody directed to von Willebrand factor antigen characterized by being capable of recognizing an epitope of the von Willebrand factor antigen, the epitope being evolutionarily conserved among vertebrate species. The antibody may bind specifically or it may bind preferably to von Willebrand factor antigen. Furthermore, the von Willebrand factor antigen may have numerous conserved epitopes present upon its surface, which may or may not be identical to one another. The antibodies may be polyclonal antibodies raised in a variety of vertebrate species. Different polyclonal antibodies raised in different species may recognize more different highly conserved epitopes than others, and thus may be more reactive or more specific than other antibodies of the subject invention from a different species, which may recognize only one conserved epitope.

The vertebrate species in which this epitope has been evolutionarily conserved are preferably warm-blooded vertebrates. Such warm-blooded vertebrates include, but are not limited to, human, canine, porcine, bovine, guinea pig, horse, cat, monkey, sheep, rat, mouse, goat, rabbit, manatee, llama, and camel. The subject invention is thus the result of the unexpected discovery and recognition that certain von Willebrand factor antigen epitopes have been highly conserved among these phylogenetically diverse species.

The antibody may be a polyclonal antibody or a monoclonal antibody. The polyclonal antibody is preferably raised in a vertebrate species and is purified by adsorption with plasma substantially free of von Willebrand factor antigen (see Example 1). In one embodiment of the subject invention the polyclonal antibody is raised in a rabbit and in another embodiment of the subject invention the polyclonal antibody is raised in a goat. The antibody of the subject invention may be a monoclonal antibody which recognizes an epitope which is evolutionarily conserved among the vertebrate species.

In using the antibody of the subject invention, the antibody in one embodiment is labeled with a detectable marker. The detectable marker is preferably an enzyme, but those skilled in the art to which the subject invention pertains would readily understand that other detectable markers may also be used. These include, but are not limited to, luminescent probes, radioisotopes, chromophores, fluorophores, or heavy metals. Preferred enzymes are horseradish peroxidase and alkaline phosphatase, although other enzymes known to those skilled in the art can also be used in the subject invention.

In one embodiment of the subject invention, the epitope which is evolutionarily conserved among vertebrate species is necessary for functioning of the von Willebrand factor. This embodiment is useful where the von Willebrand factor protein is genetically abnormal. The structure of it, i.e., the primary structure, is abnormal and causes a dysfunction of the von Willebrand factor due to a lack of or an abnormality in such a functional epitope.

These abnormalities in a functional epitope can be the result of a point mutation within the DNA sequence encoding the epitope or a point mutation somewhere else within the DNA sequence of the von Willebrand factor. The latter point mutation causes a shift in the reading frame of the genetic code encoding the von Willebrand factor, thus causing the DNA sequence encoding the functional epitope to be in an incorrect reading frame and thus the functional epitope does not function properly. These point mutations may be the result of deletions or insertions so as to create the abnormality.

The dysfunction caused by the lack of or abnormality in such a functional epitope may have clinical significance in terms of the bleeding tendency in an individual or animal. If the antibody of the subject invention recognizes a functional epitope which is conserved among vertebrate species, and is contacted with a sample containing von Willebrand factor antigen, a dysfunction in the von Willebrand factor antigen due to a lack of or an abnormality in the functional epitope results in the antibody being unable to bind or form a complex with the antigen. Therefore, the lack of a reaction between the antibody of the subject invention which recognizes the functional epitope and the von Willebrand factor antigen in the sample indicates a dysfunction in the von Willebrand factor of the subject. In this way von Willebrands disease which is caused by a dysfunction in the von Willebrand factor due to a lack of or an abnormality in a functional epitope can be diagnosed.

The subject invention further provides a first method of detecting von Willebrand factor antigen in a sample from a vertebrate species which comprises contacting the sample with the antibody of the subject invention, the antibody being directed to von Willebrand factor antigen and being characterized by being capable of recognizing an epitope of the von Willebrand factor antigen. The epitope is evolutionarily conserved among vertebrate species, and the antibody is labeled with a detectable marker. The von Willebrand factor antigen present in the sample binds to the antibody and forms a complex therewith. The antibody present in such complex, which is labeled with a detectable marker, is then detected, thus detecting the von Willebrand factor antigen in the sample. In this method, the antibody of the subject invention is actually used as a "probe" antibody to detect vWf:Ag in the sample. In a further embodiment of the subject invention, the sample itself may be insolubilized to a matrix before addition of the "probe" antibody of the subject invention. Suitable matrices include charged nylon and nitrocellulose. The antibody may be a monoclonal antibody of the subject invention or a polyclonal antibody of the subject invention.

This method can be used, for example, for blots of whole blood or blots of plasma which are probed with an antibody of the subject invention. A color reaction is looked for on the dry spots of the blots. An indicator is used to detect the reaction. The antibody of the subject invention can further be used to produce an insoluble reaction product relative to molecular size-fractionated von Willebrand factor on a nitrocellulose membrane. The sample material is separated in agarose and transferred to nitrocellulose, the western blot technique, and the transfer bands are then probed with the antibody of the subject invention.

The subject invention further provides a second method of detecting von Willebrand factor antigen in a sample from a vertebrate species which comprises contacting the sample with an antibody of the subject invention, the antibody being directed to von Willebrand factor antigen and being characterized by being capable of recognizing an epitope of the von Willebrand factor antigen, the epitope being evolutionarily conserved among vertebrate species. The von Willebrand factor antigen in the sample binds to the antibody and forms a complex therewith. The complex so formed is then contacted with a second antibody of the subject invention, this second antibody being labeled with a detectable marker. This forms a second complex which includes the antibody initially contacted with the sample, the von Willebrand factor antigen, and the second antibody. The second antibody present in the second complex which is thus formed, being labeled with a detectable marker, is then detected thus detecting the von Willebrand factor antigen in the sample. The antibody may be a monoclonal antibody or a polyclonal antibody, and the second antibody may also be a monoclonal antibody or a polyclonal antibody.

The subject invention further provides a third method of detecting von Willebrand factor antigen in a sample in a vertebrate species which comprises contacting a sample with an antibody of the subject invention, the antibody being directed to von Willebrand factor antigen and being characterized by being capable of recognizing an epitope of the von Willebrand factor antigen, the epitope being evolutionarily conserved among vertebrate species. The von Willebrand factor antigen in the sample binds to the antibody and forms a complex therewith. The complex thus formed is then contacted with a second antibody of the subject invention so as to form a second complex which includes the antibody initially contacted with the sample, the von Willebrand factor antigen, and the second antibody. This second complex which is thus formed is then contacted with a third antibody, the third antibody being directed to the second antibody and being labeled with a detectable marker, so as to form a third complex which includes the antibody initially contacted with the sample, the von Willebrand factor antigen, the second antibody, and the third antibody. The third antibody present in the third complex thus formed, which is labeled with a detectable marker, is then detected thus detecting the von Willebrand factor antigen in the sample.

In these second and third methods where two antibodies of the subject invention are used, the epitopes which are recognized by each of these antibodies may be the same or different. In the first case, the epitope will be the same only if at least two copies of the epitope are found on the von Willebrand factor antigen. This would be the only configuration which would allow a complex to be formed as described in the assay configuration. If only one copy of the epitope is present on the von willebrand factor antigen, then the second antibody must recognize a different conserved epitope than the first antibody.

In a preferred embodiment of the third method, the antibody which is initially contacted with the sample may be a monoclonal antibody or a polyclonal antibody which is raised in a vertebrate species. Although the polyclonal antibody can be raised in numerous vertebrate species, preferred vertebrate species include rabbit and goat.

The second antibody which is used in the preferred third method may also be a monoclonal antibody or a polyclonal antibody which is raised in a vertebrate species. Once again, although the polyclonal antibody can be raised in various different vertebrate species, the preferred vertebrate species are rabbit and goat.

In this preferred embodiment of the subject invention, the vertebrate species from which the sample to be tested is obtained is different from the vertebrate species in which the polyclonal antibody which is initially contacted with the sample is raised.

Those skilled in the art would recognize this method as being a modified double sandwich assay. The antibody which is initially contacted with the sample is termed a capture antibody, the second antibody is termed a sandwich antibody, and the third antibody is termed a detectant antibody. Using these terms, the preferred embodiment of the subject invention involves a polyclonal antibody which is a capture antibody and is raised in a rabbit and the sample is from a vertebrate species other than rabbit. Alternatively, the invention may comprise a polyclonal antibody which is the capture antibody and is raised in a goat, and the sample is from a vertebrate species other than goat.

Additionally, it is desirable that the capture antibody and the sandwich antibody be raised in different vertebrate species, so that the detectant antibody does not react with the capture antibody. In one embodiment of the subject invention, the capture antibody is raised in a goat and the sandwich antibody is raised in a rabbit. Alternatively, the capture antibody may be raised in a rabbit and the sandwich antibody may be raised in a goat.

For example, if rabbit anti-dog is used as a coating antibody, the sample is goat von Willebrand factor antigen, the sandwich antibody is goat anti-dog, and the indicator antibody is pig anti-goat IgG, this assay configuration allows recognition of the conserved epitopes on the goat von Willebrand factor antigen. However, if the coating antibody is a goat anti-dog, the sample is goat von Willebrand factor antigen, the sandwich antibody is rabbit anti-dog, and the indicator is goat anti-rabbit, this assay configuration does not allow recognition of the conserved epitopes on the goat von Willebrand factor antigen. These examples illustrate that the capture antibody and the von Willebrand factor antigen in this assay configuration must be from different species.

As indicated above, the capture and the sandwich antibodies must be from different species in order to enable the use of an indicator (detectant) antibody which will not attach to the capture antibody, since the capture antibody is attached to an immunological reaction surface. The sandwich antibody and the von Willebrand factor antigen can be of the same species. These configurations indicate that when the antibody of the subject invention is used as a coating antibody, it will not recognize von Willebrand factor antigen which is from the same species it was raised in. However, a sandwich antibody of the subject invention will recognize von Willebrand factor antigen from the same vertebrate species from which it was raised in, if the von Willebrand factor antigen is in the solid phase, i.e. it is already bound to the capture antibody.

It is possible to use a polyclonal capture antibody without adsorbing it first, but this decreases the capability to detect low levels of plasma von Willebrand factor antigen due to background adsorbances. A polyclonal antibody has a 30 fold loss in assay sensitivity from 0.0004 units/ml to 0.00125 units/ml when it is adsorbed versus unadsorbed, respectively.

The sandwich antibody cannot be used without the adsorption step. Preferably the capture and sandwich antibodies are both adsorbed in order to increase the sensitivity of quantatitatively determining the amount of von Willebrand factor antigen in plasma.

In each of the methods discussed above, the antibody which is initially contacted with the sample may be attached to an immunological reaction surface. An immunological reaction surface is a surface which is insoluble in the reacting medium and on which immunological reactions take place, for example reactions involved in the ELISA procedure. Typically they are glass, paper, or plastic, such as polystyrene or polyacrylate. The surface may be the interior surface of a test tube, the well of a microtiter plate or some other container suitable for an immunological reaction. Those skilled in the art will know of other appropriate surfaces on which an immunological reaction can take place and which can be used in the subject invention, e.g. glass or plastic beads or rods, or paper strips. For purposes of the subject invention, such an immunological reaction surface will be one to which the antibodies of the subject invention will adhere.

Immunological reaction conditions for the disclosed methods . are conditions with respect to temperature, concentration, solvent, pH, etc. under which the immunological reaction such as the formation of an antibody/antigen complex will take place. Those skilled in the art are thoroughly familiar with the parameters under which such complexes will form. They will know that the temperature cannot be so high or the pH so extreme as to inactivate the reactant. The solvent is typically a selected buffer or other carrier for the reactants. It may be plasma, serum or some fraction of these materials. The reaction products, including the intermediate reaction products of this invention, are soluble in the reaction solvent. Any suitable immunological reaction conditions which allow the recognition of the conserved epitopes by the antibodies of the subject invention may be used in the methods of the invention.

In each of the methods disclosed above, the detectable marker is preferably an enzyme, but those skilled in the art to which the subject invention pertains would readily understand that other detectable markers may also be used. These include, but are not limited to, luminescent probes, radioisotopes, chromophores, fluorophores, or heavy metals. Preferred enzymes are horseradish peroxidase and alkaline phosphatase, although other enzymes known to those skilled in the art can also be used in the subject invention.

Although the procedure of the invention will be specifically described for purposes of illustration utilizing a detector anti-immunoglobulin (IgG) conjugated with horseradish peroxidase and using orthophenylenediamine dihydrochloride color reagent, other detector reagents can also be employed. These include, for example, tetramethyl benzidine as a peroxidase substrate. An effective and convenient substrate for alkaline phosphatase is paranitrophenyl phosphate (PNPP) which, like OPD, is available commercially in tablet form. The enzyme reaction of alkaline phosphatase and PNPP can be stopped with concentrated NaOH, and the yellow color is quite stable and can be assessed visually or photometrically at 405 nm. Other compounds of this class having the appropriate molar absorptivity and solubility characteristics are also appropriate substrates.

Immunoglobulin linked to N-hydroxysuccinimidobiotin (i.e., biotin) can also be effective probes for anti vWf:Ag when reacted with a detector (avidinhorseradish peroxidase). The peroxidase substrates identified above would be used to generate the color endpoint.

The color detectors are most convenient for utilizing the anti-vWf:Ag of the invention, but the invention is not so limited. Other detection systems including radioisotopic, luminescent, or electrochemical labels can also be employed.

The samples which can be analyzed using the methods of the subject invention can be obtained from any vertebrate species in which one is interested in determining the von Willebrand factor antigen content of the sample. Preferably, the vertebrate species is a warm-blooded vertebrate species. Such warm-blooded vertebrate species include, but are not limited to, human, canine, porcine, bovine, guinea pig, horse, cat, monkey, sheep, rat, mouse, goat, rabbit, manatee, llama, and camel.

The sample which is analyzed using the subject invention is preferably a biological fluid. Suitable biological fluids include serum, plasma, cell lysates, urine, or even secreted products from a tissue culture cell. A person skilled in the art to which the subject invention pertains would readily understand that numerous other biological fluids from the vertebrate species can be used as samples in the subject assay. In preferred embodiments of the subject invention, however, the biological fluid comprises serum or plasma, with the most preferred biological fluid comprising plasma.

Numerous types of assays can be used in the subject invention as long as the configuration of the assay allows the antibody to recognize the conserved epitope, although the preferred embodiment of the subject invention comprises using the modified double sandwich ELISA assay which allows the antibody of the subject invention to recognize the conserved epitopes. Those skilled in the art to which the subject invention pertains would readily understand that any conventional immunoassay which would allow the recognition of the conserved epitope can be used in the subject invention to both quantitatively and qualitatively detect von Willebrand factor antigen in multiple vertebrate species. Such other assays includes regular sandwich assays, which are discussed above, wherein an antigen is sandwiched between the bound antibody on a solid carrier and a labeled antibody, reverse sandwich assays, in which a labeled antibody is reacted with the antigen prior to contact with the bound antibody, and a simultaneous sandwich assay, in which the antibodies and the antigen are reacted simultaneously. These other immunoassay methods can be used with the antibodies of the subject invention if they allow recognition by the antibodies of the conserved epitopes.

As discussed above, if the epitope which is recognized by the antibody of the subject invention is necessary for the functioning of von Willebrand factor, such an antibody can be used in the method of the subject invention to detect dysfunctional von Willebrand factor in the subject, the dysfunction being due to a lack of or an abnormality in the functional epitope in the von Willebrand factor. Specifically, the method comprises obtaining a sample of plasma containing the von Willebrand factor from the subject and detecting the von Willebrand factor antigen in the sample using one of the methods disclosed above.

With an antibody of the subject invention which recognizes the functional epitope, if no or substantially no von Willebrand factor antigen is detected in the sample it is an indication that the functional epitope is lacking or abnormal and thus indicates that dysfunctional von Willebrand factor due to a lack of or abnormality in the functional epitope is present in the subject.

This method can be used to diagnose von Willebrands disease caused by dysfunctional von Willebrand factor in a vertebrate species.

The subject invention further provides a kit for use in qualitatively detecting von Willebrand factor antigen in a test sample from a vertebrate species which comprises an amount of an antibody directed to von Willebrand factor antigen characterized by being capable of recognizing an epitope of the von Willebrand factor antigen, the epitope being evolutionarily conserved among vertebrate species and the antibody being labeled with a detectable marker. The kit also includes a positive control sample (one standard sample having a known . von Willebrand factor antigen concentration) and a negative control sample (a sample substantially free of von Willebrand factor antigen).

Further provided is a kit for use in qualitatively detecting von Willebrand factor antigen in a test sample from a vertebrate species which comprises:
(A) an amount of a first antibody directed to von Willebrand factor antigen characterized by (i) being capable of adhering to an immunological reaction surface, and (ii) being capable of recognizing an epitope of the von Willebrand factor antigen, the epitope being evolutionarily conserved among vertebrate species;
(B) an amount of a second antibody directed to von Willebrand factor antigen characterized by being capable of recognizing an epitope of the von Willebrand factor antigen, the epitope being evolutionarily conserved among vertebrate species and the second antibody being labeled with a detectable marker;
(C) one standard sample having a known von Willebrand factor antigen concentration; and
(D) a control sample substantially free of von Willebrand factor antigen.

Further provided is a kit for use in qualitatively detecting von Willebrand factor antigen in a test sample from a vertebrate species which comprises:
(A) an amount of a first antibody directed to von Willebrand factor antigen characterized by (i) being capable of adhering to an immunological reaction surface, and (ii) being capable of recognizing an epitope of the von Willebrand factor antigen, the epitope being evolutionarily conserved among vertebrate species;
(B) an amount of a second antibody directed to von Willebrand factor antigen characterized by being capable of recognizing an epitope of the von Willebrand factor antigen, the epitope being evolutionarily conserved among vertebrate species;
(C) an amount of a third antibody directed to the second antibody of step (B) and labeled with a detectable marker;
(D) one standard sample having a known von Willebrand factor antigen concentration; and
(E) a control sample substantially free of von Willebrand factor antigen.

The subject invention also provides a kit for use in quantitatively determining the amount of the von Willebrand factor antigen in a test sample from a vertebrate species which comprises:
(A) an amount of an antibody directed to von Willebrand factor antigen characterized by being capable of recognizing an epitope of the von Willebrand factor antigen, the epitope being evolutionarily conserved among vertebrate species and the antibody being labeled with a detectable marker;
(B) a series of standard samples having a known von Willebrand factor antigen concentration; and
(C) a control sample substantially free of von Willebrand factor antigen.

Further provided is a kit for use in quantitatively determining the amount of von Willebrand factor antigen in a test sample from a vertebrate species which comprises:
(A) an amount of a first antibody directed to von Willebrand factor antigen characterized by (i) being capable of adhering to an immunological reaction surface, and (ii) being capable of recognizing an epitope of the von Willebrand factor antigen, the epitope being evolutionarily conserved among vertebrate species;
(B) an amount of a second antibody directed to von Willebrand factor antigen characterized by being capable of recognizing an epitope of the von Willebrand factor antigen, the epitope being evolutionarily conserved among vertebrate species and the second antibody being labeled with a detectable marker;
(C) a series of standard samples having a known von Willebrand factor antigen concentration; and
(D) a control sample substantially free of von Willebrand facto antigen.

A kit is also provided by the subject invention for use in quantitatively determining the amount of von Willebrand factor antigen in a test sample from a vertebrate species which comprises:

(A) an amount of a first antibody directed to von Willebrand factor antigen characterized by (i) being capable of adhering to an immunological reaction surface, and (ii) being capable of recognizing an epitope of the von Willebrand factor antigen, the epitope being evolutionarily conserved among vertebrate species;

(B) an amount of a second antibody directed to von Willebrand factor antigen characterized by being capable of recognizing an epitope of the von Willebrand factor antigen, the epitope being evolutionarily conserved among vertebrate species;

(C) an amount of a third antibody directed to the second antibody of step (B) and labeled with a detectable marker;

(D) a series of standard samples having a known von Willebrand factor antigen concentration; and (E) a control sample substantially free of von Willebrand factor antigen.

As discussed above, where two antibodies of the subject invention are provided in the kits, the epitopes which are recognized by each of the antibodies may be the same or different.

In each of these kits which can be used for qualitative and/or quantitative detection of von Willebrand factor antigen in a test sample, the antibody, excluding the third antibody referred to in these methods, is preferably a monoclonal antibody or a polyclonal antibody raised in a vertebrate species. Although numerous vertebrate species can be used to raise the polyclonal antibodies, the preferred vertebrate species are rabbit and goat.

When a third antibody is present in the kit as discussed above, the preferred antibody is a polyclonal antibody raised in a goat, the preferred second antibody is a polyclonal antibody raised in a rabbit, and the preferred third antibody is anti-rabbit IgG.

In another embodiment of the subject invention, the kit which uses the third antibody preferably comprises a first antibody which is a polyclonal antibody raised in a rabbit, a second antibody which is a polyclonal antibody which is raised in a goat, and a third antibody which is anti-goat IgG.

In each of these kits discussed above, the detectable marker is preferably an enzyme, but those skilled in the art to which the subject invention pertains would readily understand that other detectable markers may also be used. These include, but are not limited to, luminescent probes, radioisotopes, chromophores, fluorophores, or heavy metals. Preferred enzymes are horseradish peroxidase and alkaline phosphatase, although other enzymes known to those skilled in the art can also be used in the subject invention.

By using the kits of the subject invention one is enabled to quantitatively determine the amount of von Willebrand factor antigen in a test sample from a vertebrate species.

Where the kit contains one antibody of the subject invention, a method of quantitatively determining the amount of von Willebrand factor antigen in a test sample from a vertebrate species using the kit comprises:

(A) separately contacting each of the test sample, the standard samples, and the control sample with the antibody such that any von Willebrand factor antigen in each of the samples binds to the antibody and each forms a complex therewith;

(B) separately detecting the amount of antibody present in each of the complexes formed in step (A), thus detecting the von Willebrand factor antigen in each of the test sample, standard samples, and control sample; and (C) comparing the amount of antibody present in each of the test sample, standard samples, and control sample to quantitatively determine the amount of von Willebrand factor antigen in the test sample.

Where the kit includes a first and a second antibody as discussed above, the first antibody being the antibody initially contacted with the sample, the kit can be used in a method of quantitatively determining the amount of von Willebrand factor antigen in the test sample from a vertebrate species which comprises:

(A) separately contacting each of the test sample, the standard samples, and the control sample with the first antibody such that any von Willebrand factor antigen in each of the samples binds to the first antibody and each forms a complex therewith;

(B) separately contacting each of the complexes formed in step (A) with the second antibody so as to form a second complex for each which includes the first antibody, the von Willebrand factor antigen, and the second antibody;

(C) separately detecting the amount of second antibody present in each of the second complexes formed in step (B), thus detecting the von Willebrand factor antigen in each of the test sample, standard samples, and control sample; and (D) comparing the amount of second antibody present in each of the test sample, standard samples, and control sample to quantitatively determine the amount of von Willebrand factor antigen in the test sample.

Where the kit includes a first, second and third antibody, as discussed above, the kit can be used in a method of quantitatively determining the amount of von Willebrand factor antigen in a test sample from a vertebrate species which comprises:

(A) separately contacting each of the test sample, the standard samples, and the control sample with the first antibody such that any von Willebrand factor antigen in each of the samples binds to the first antibody and each forms a complex therewith;

(B) separately contacting each of the complexes formed in step (A) with the second antibody so as to form a second complex for each which includes the first antibody, the von Willebrand factor antigen, and the second antibody;

(C) separately contacting each of the second complexes formed in step (B) with the third antibody so as to form a third complex for each which includes the first antibody, the von Willebrand factor antigen, the second antibody, and the third antibody;

(D) separately detecting the amount of third antibody present in each of the third complexes formed in step (C), thus detecting the von Willebrand factor antigen in each of the test sample, standard samples, and control sample; and (E) comparing the amount of third antibody present in each of the test sample, standard samples, and control sample to quantitatively determine the amount of von Willebrand factor antigen in the test sample.

The various reactants and reagents employed in the practice of this invention may be conveniently provided in these kits suitable for use by the physician or veterinarian, or for use in clinical and research laboratories. One preferred kit will contain a capture antibody of the invention together with a sandwich antibody and a detector IgG together with at least one plasma of known vWf:Ag concentration, e.g. the 65% standard plasma or 83% reference plasma described in Example 1 together with an abnormal control plasma, i.e. a substantially 0% vWf:Ag plasma. If the test is intended for quantitative se, it will additionally contain a sufficient number of standard plasmas to construct a reference curve. For example, it could contain a 15%, 30% and 45% plasma. Either of the kits may also contain an internal normal control plasma of known concentration which can be used to confirm the integrity of the system. The kit will also contain a detector IgG which will react with the sandwich antibody under immunological reaction conditions.

One very convenient form of kit for use of the invention comprises a microtiter plate with an antibody of the invention adhered to the surface of each well.

Additional reagents utilized in the practice of the invention may be provided in the kit, but most conveniently will be maintained as stock reagents in the laboratory. These include dilution buffer, washing buffer, citrate buffer, OPD or similar detectors, dilute sulfuric acid and hydrogen peroxide.

In the examples that follow, Example 1 describes a first embodiment of the subject invention where the antibody which recognizes an evolutionarily conserved epitope is a polyclonal antibody raised in a vertebrate species, preferrably rabbits or goats. The polyclonal antibody is raised in response to vWf:Ag from canines and is also referred to as anti-canine von Willebrand factor antigen (anti-canine vWf:Ag). The polyclonal antibody is used in an assay which is one embodiment of the subject invention, a modified double sandwich ELISA assay, to qualitatively and quantitatively detect von Willebrand factor in a variety of vertebrate species.

Example 2 provides numerous additional embodiments of the subject invention wherein the antibody which recognizes an evolutionarily conserved epitope is a polyclonal antibody raised in one of several vertebrate species, or a monoclonal antibody. The antibodies are raised in response to vWf:Ag from a variety of vertebrate species in addition to canines. As in Example 1, the antibodies of the Example 2 are used in an assay which is one embodiment of the subject invention, a modified double sandwich ELISA assay, to qualitatively and quantitatively detect von Willebrand factor in a variety of vertebrate species. The antibodies of the subject invention, when used in an assay which allows the antibody to recognize the evolutionarily conserved epitopes of von Willebrand factor antigen, results in an assay which allows the qualitative and quantitative detection of von Willebrand factor antigen in numerous vertebrate species.

The assay disclosed in the Examples is a modified double sandwich ELISA assay, but those skilled in the art will readily understand that any immunoassay configuration which allows the antibodies to recognize the conserved epitopes of von Willebrand factor antigen can be used in the present invention.

These and other embodiments of the subject invention are more fully described in the examples hereinafter.

EXAMPLE 1

Use of Canine vWf Antibodies To Detect vWf In Multiple Vertebrate Species

Novel antibodies have now been discovered which can be used in the ELISA procedure to test for the presence and concentration of vWf:Ag in a wide variety of species. These antibodies are raised against canine vWf:Ag and purified by adsorption with the plasma proteins of canines homozygous for vWd. Canines homozygous for vWd, or type III vWd, have no vWf antigen. The purified antibodies can be employed qualitatively or semiquantitatively in screening tests for vWf:Ag or for sensitive and specific quantitative determination of this protein in vertebrates such as mammals, including humans. The antibodies may be provided in a variety of kits which may additionally contain associated reactants, normal and abnormal comparison plasmas and standards.

It is essential for one embodiment of the subject invention to employ antibodies which will adhere or stick to an insoluble substrate surface, e.g. the surface of the microtiter plate wells or other container in which the test is carried out. The antibodies of this embodiment of the invention are sticky proteins which will adhere firmly to the substrate surface. So far as is known, no antibodies to canine vWf:Ag have heretofore been known which are sufficiently sticky for use in a highly sensitive and accurate ELISA procedure.

The antibodies of this embodiment of the invention are sticky polyclonal antibodies raised against canine vWf:Ag, but reactive with vWf:Ag from other vertebrate species, purified by adsorption with the plasma proteins from dogs homozygous for vWd. The antibodies are useful in methods for determining the presence and quantity of vWf:Ag in vertebrate plasma by contacting the antibody with the plasma to be tested in a reaction mixture under immunological reaction conditions and thereafter determining if an immunological reaction, i.e. a reaction between the antibody (anti-vWf:Ag) and antigen (vWf:Ag) in the plasma has taken place by an appropriate procedure.

The extent of the immunological reaction can be determined qualitatively or semiquantitatively by visual comparison of the optical density of unknown samples with known standards or quantitatively by spectrophotometric comparison with standard curves prepared using a number of samples of known vWf:Ag concentration.

One embodiment for carrying out the process of this invention is:
1. Utilizing purified canine vWf:Ag, raise antibodies to canine vWf:Ag (hereinafter, anticanine vWf:Ag) in selected vertebrate species such as rabbits or goats.
2. Coat the surface of the reaction vessel, suitably the well of a microtiter plate, with the anticanine vWf:Ag to serve as the capture, immobilizing or anchor antibody.
3. Add the test plasma containing an unknown quantity of vWf:Ag to the test vessel.
4. Add a second anticanine vWf:Ag to the vessel. This is the sandwich antibody and should be different from the capture antibody, i.e. raised in a different species. For example, if the capture antibody is raised in a rabbit, the sandwich antibody may be raised in a goat, or vice versa.

5. Add a detectant for the sandwich antibody, for example, an enzyme-conjugated anti IgG to the reaction vessel. This reagent should be reactive with the sandwich antibody used in step 4 (i.e. raised against the same species), but not reactive with the capture antibody. For example, it should be antigoat IgG if the sandwich antibody was raised in a goat.
6. Detect the amount of vWf:Ag in the unknown plasma by measuring the amount of antibody-conjugated detectant. For example, if the detectant is an enzyme which produces a color reaction, the intensity of the color, i.e. the optical density of the color produced, can be utilized to determine the amount of vWf:Ag in the unknown either qualitatively or quantitatively.

This embodiment is a modified ELISA procedure. Those skilled in the art will recognize that the generalized outline omits certain of the specific steps such as serial dilution and washing with appropriate buffers which are standard in the ELISA procedure. Although specific buffers and other reagents will be described hereinafter, and specific dilutions will be emloyed to illustrate the invention, the skilled artisan will recognize that these are illustrative only and that many equivalents are possible.

The operation of this invention, especially in the qualitative (i.e. screening) mode requires the selection of a standard vWf:Ag concentration to which one or more concentrations of known standards and the plasma, the concentration of which is to be determined, will be compared. The standard may be prepared as described below.

A convenient single standard is 65% (0.65 unit/ml) of the plasma vWf:Ag level of healthy individuals (hereinafter called normal plasma and assigned a value of 100% or 1 u/ml), which may be selected for purposes of comparison with other plasmas. The assay can be made semiquantitative or quantitative by selecting several reference standards having vWf:Ag levels such as 15% (0.15 u/ml), 35% (0.35 u/ml), and 65% (0.65 u/ml) of normal. These levels are selected for the presently preferred practice of the invention because extensive experience with EIA testing of healthy individuals of several species has indicated that the lower limit for the normal range is about 60% (0.6 u/ml). A person or animal is statistically at low risk for bleeding during surgery or other stress situations and is unlikely to transmit vWd to progeny if the level of vWf:Ag is at least 60% (0.6 u/ml). Individuals with levels of less than 60% (0.6 u/ml) require special caution. The methods of this invention are useful in genetic surveillance in a breeding program to reduce or eliminate the prevalence of vWd in various animal species such as dogs, cats, horses, nonhuman primates, and other domestic, laboratory or exotic animals.

ISOLATION AND PURIFICATION OF CANINE vWf:Ag

The vWf:Ag was purified by cryoconcentration and molecular exclusion chromatography. The procedures are generally well known in the art. Canine blood was collected in 3.8% trisodium citrate (10% V/V) and the plasma was made cell-free by centrifugation at 2,000 and 12,000 x g. The plasma wa stored in 100 ml aliquots at −40° C. until used.

Four 100 ml aliquots were thawed slowly overnight at 4° C. The following morning the plasma with the suspended cryoprecipitate was dispensed in 40 ml aliquots in Nalgene test tubes and 53% ethanol was added and mixed to a final concentration of 3%. The tubes were placed in a methanol-water ice bath at −3° C. for 30 minutes and then centrifuged at 12,000 x g for 10 min. at 4° C. The supernatant plasma was discarded and the precipitate taken up in 3 ml of phosphate buffered saline (PBS), pH 7.4.

This concentrate was further purified by loading on a 2.5×40 cm 2% agarose column and elution at 20 ml/hr at room temperature with PBS into 5 ml fractions which were stored at 4° C. The fractions were analyzed for vWf:Ag by EIA overnight and the four peak fractions, typically containing 10–12 u/ml vWf:Ag were pooled and filtered over a 2.5×40 cm 6% agarose column, eluted as above. The five peak fractions, usually containing in excess of 5 u/ml of purified vWf:Ag, were pooled, dispensed in 0.5 ml aliquots, and stored at −40° C.

IMMUNIZATION OF VERTEBRATES (RABBITS OR GOATS) WITH CANINE vWf:Ag: PREPARATION OF HETEROLOGOUS ANTICANINE vWf:Ag

Antisera to canine vWf:Ag were raised in Chinchilla-Flemish Giant NYS:(FG) rabbits and a pooled Alpine grade goat. Aliquots of the purified antigen prepared as described above were thawed and mixed with an equal volume of 2% Al(OH)$_3$ diluted 1:10 with sterile saline. The fur on each 3-6 month old rabbit's back was clipped and the area thoroughly cleaned before each inoculation. A loading dose of 2 ml of the vWf:AgAl(OH)$_3$ mixture was injected intradermally in several sites, followed by serial booster doses of 1 ml at weekly intervals for 4 weeks. Five weeks after the loading dose, 50 ml of rabbit blood were collected by ear artery puncture and then serum harvested as described below.

Antiserum was also raised in a single 4-year-old goat. Four ml of the purified vWf:Ag was mixed with an equal volume of Al(OH)$_3$ as above and injected intradermally into the clipped back of the goat. The goat was immunized at half the loading dose seven additional times over a period of two months and 400 ml of blood were collected by jugular puncture.

The goat and rabbit blood were separately collected in 16×125 mm glass tubes and clotted at 37° C. for one hour and overnight at 4° C. The contracted red cell clots were detached and the serum decanted and centrifuged to remove residual cells. The goat and rabbit antisera thus prepared were each incubated at 56° C. to inactivate complement and residual coagulation factors were adsorbed with Ca$_3$(PO$_4$)$_2$ (10 mg/ml) to provide antisera ready for the next adsorption step to prepare the antibodies of the invention.

ADSORPTION OF ANTISERA

Citrated canine plasma from dogs homozygous for vWd was used to prepare a cryoprecipitate free of vWf:Ag for use as an adsorbent for equal volumes of the antisera prepared in the previous step. The antiserum (rabbit or goat) was added to the cryoprecipitate and incubated for one hour at 37° C. and overnight at 4° C. The adsorbed antiserum was centrifuged at 10,000 g for about 10 minutes at 4° C. the following day to remove precipitated material. Each antiserum was adsorbed a second time with an equal volume of adsorbent to prepare a serum from which contaminant precipitable antibodies were removed and other contaminant antibodies neutralized.

Each serum thus prepared contains antibody of the invention and is employed in the following purification step.

In order to obtain or make the polyclonal antibodies of the subject invention, the adsorption step is required which utilizes plasma from dogs homozygous for vWd to purify antibodies of the subject invention. These dogs have type III vWd and have no von Willebrand factor antigen. Although plasma from dogs homozygous for vWd is preferred, those skilled in the art to which the subject invention pertains would understand that other plasma homozygous for vWd from other species, i.e. human or bovine, could also be used for the adsorption step. The only requirement would be that the non-specific antibodies substantially cross react with the non-von Willebrand factor proteins present in the human or porcine homozygous vWd plasmas being used for the adsorption.

One way to identify dogs whose plasma is suitable for the adsorption step is to screen a number of dogs using a standard Laurell assay for vWf:Ag. The Laurell assay is well known in the art and has been used routinely to detect vWf:Ag in canines (1,39,40). Samples from those dogs found to be negative for vWf:Ag using the Laurell assay should then be retested using an immunoradiometric assay, which has a much lower limit of detection. This will confirm that the dog is actually vWf:Ag negative, and is a type III vWd dog whose plasma can be used for the adsorption step. Suitable immunoradiometric assays are those routinely performed in sophisticated human hospital laboratories, the methods of which are well known in the art (38). A negative vWf:Ag result in the immunoradiometric assay confirms that plasma from the dog tested can be used for the adsorption step.

Another way to obtain plasma which is suitable for the adsorption step is to adsorb plasma with a cryoprecipitate supernatant. This method was routinely used before assays which could identify dogs homozygous for vWd were devised (1). Briefly, concentrated plasma is precipitated using 3% ethanol so as to form a cryoprecipitate. The cryoprecipitate is placed on an agarose column which purifies proteins based on their molecular size. von Willebrand factor is a very large protein and therefore it elutes first on the agarose column. The proteins remaining after the vWf has eluted are the "contaminating proteins" other than vWf.

A further wa to obtain plasma which is suitable for the adsorption step is to make a 3% ethanol cryoprecipitate as above and save the supernatant. Due to its large size, the vWf protein is present in the precipitate and not in the saved supernatant. The saved supernatant is frozen and then slowly thawed, and another cryoprecipitate is formed by increasing the ethanol to 10%. The resulting supernatant is depleted of vWf but contains the contaminating proteins necessary for the adsorption step. Each of the above adsorption methods is well known in the art (1).

Additionally, colonies of dogs known to be homozygous for vWd are located, for example, at the Veterinary Hematology Laboratory of the New York State Department of Health in Albany, N.Y. and at the University of North Carolina at Chappell Hill, N.C.

In regard to the monoclonal antibodies of the subject invention, they can be obtained using standard methods. Standard methods for producing monoclonal antibodies in vitro and for screening such monoclonal antibodies are well known in the art to which the subject invention pertains (41). Once obtained using these known procedures, the monoclonal antibodies which recognize a conserved epitope of the vWf:Ag can be used just as the polyclonal antibodies of the subject invention. The monoclonal antibodies of the subject invention may be used in combination with other different monoclonal antibodies of the subject invention to detect vWf:Ag using any of the methods disclosed herein. By combining the various monoclonal antibodies, each of which recognizes a conserved epitope, the sensitivity and specificity of the assay is increased by increasing the likelihood that one or more of the different monoclonal antibodies will recognize a conserved epitope and be capable of reacting with that epitope.

PURIFICATION OF ANTICANINE vWf:Ag

The preparations of the previous step were precipitated three times with half saturation of aqueous $(NH_4)_2SO_4$ to produce phosphate buffered saline (PBS) globulins. The globulins were extensively dialyzed versus PBS and then 0.01M Tris buffer (pH 8.0) to remove residual $(NH_4)_2SO_4$. Approximately 100 mg. of globulin fraction, after dialysis, was applied to a 2.5 ×40 cm DEAE Sepharose column and eluted with a gradient of 0.01M Tris-HCl, pH 8.0, and ending with the same buffer containing 0.3M sodium chloride (ph 8.0). The peak fractions containing the heterologous rabbit or goat anticanine vWf:Ag IgG were identified in the EIA (Laurell rocket assay) or the ELISA assay respectively using normal canine and homozygous canine vWd plasmas.

The peak fractions thus prepared contain the purified antibodies of the invention. The fractions can be used directly in the process of the invention.

EVALUATION OF SPECIFICITY OF IgG FOR CANINE vWf

The rabbit IgG containing antibodies to canine vWf:Ag was evaluated for specificity by being cast in agarose gels and generating precipitin rockets in the EIA against normal canine plasma, but failing to generate detectable precipitin reactions against plasma from dogs homozygous for vWd. The immune goat IgG to canine vWf:Ag did not form precipitin rockets against normal canine plasma in the EIA, thereby demonstrating the differing physicochemical properties of these two novel antibodies to the same protein. However, when microtiter plates were coated initially with the rabbit anticanine vWf:Ag IgG and the goat anticanine vWf:Ag IgG was used as the second (sandwich) antibody, normal dog plasma strongly reacted whereas plasma from dogs homozygous for vWd failed to react and behaved like the buffer blanks. Antisera which were not adsorbed with homozygous vWd plasma prior to evaluation by this ELISA assay generated optical density readings higher than the buffer blanks (i.e. contained non-vWf contaminants).

The antibodies of the invention from different species, therefore, differ to some extent in physicochemical properties. However, they react similarly in the ELISA assay with canine plasma to detect vWf:Ag.

PREPARATION OF BUFFERS AND OTHER REAGENTS

Coating Buffer - (10x stock solution) - Dilute 1:10 before use

PREPARATION OF BUFFERS AND OTHER REAGENTS -continued

| | |
|---|---|
| 21.2 g Na$_2$CO$_3$ | 0.01 g Thimerosal (Bacteriostat) check pH equals 9.6 - adjust with NaOH or HCl |
| 33.6 g NaHCO$_3$ | dilute up to 1.0 liter |
| Buffer Added After Coating | |
| 4.5 g NaCl in 450 ml distilled water | |
| 0.5 mg Thimerosal | |
| 1000 mg bovine serum albumin (BSA) | |
| adjust to pH 7.4 using 1 mole/1 Tris base | |
| dilute up 0.5 liter (500 ml) | |
| PBS-Tween Buffer - (10x stock solution) - Dilute 1:10 before use | |
| 80.1 g NaCl | 50 ml Tween 20 |
| 2.0 g KCl | 10 mg Thimerosal |
| 9.46 g Na$_2$HPO$_4$ | check pH - adjust to 7.4 with NaOH or HCl |
| 2.0 g KH$_2$PO$_4$ | dilute up to 1.0 liter |
| ELISA Dilution Buffer (10x-Stock) Dilute 1:10 and pH to 7.4 with 1 molar Tris-base (approximately 3.0 ml) | |
| 90.0 g NaCl | |
| 5.0 g BSA | |
| 10 mg Thimerosal | |
| 10.6 g disodium EDTA (FW 372.24) | |
| dilute to 1 liter | |
| Citrate Buffer - (10x stock solution) - Dilute 1:10 before use | |
| 63.6 citric acid | check pH equals 5.0 - adjust with NaOH or HCl |
| 97.1 g Na$_2$HPO$_4$ | dilute up to 1.0 liter |
| 0.01 g Thimerosal | |
| Ortho-Phenylenediamine (OPD) - Substrate Solution - Make fresh just before use. | |
| 30 mg OPD tablet (Sigma Chemical Co., St. Louis, Mo.) | |
| 33 ml citrate buffer | |
| 150 µl of 3% H$_2$O$_2$ | |
| Sulfuric Acid (H$_2$SO$_4$) 4.5 mole/1 | |
| 125 ml concentrated H$_2$SO$_4$ added slowly to 375 ml of water | |
| Tris Base 1 mole/1 | |
| 121.1 g Tris-base diluted up to 1.0 liter | |

QUALITATIVE AND SEMIQUANTITATIVE ELISA SCREENING PROCEDURES

Strip Preparation: Test strips (e.g., Duo-Strips containing eight wells available from Dynatech corporation, Alexandria, VA) are coated with 100 µl/well of capture (.e.g rabbit) antibody to canine vWf:Ag appropriately diluted (e.g. 1:500) with coating buffer. Coating is usually completed for many strips at once. The strips are stacked and incubated overnight in a humid 37° C. incubator. The top strips are covered by tape. The following day, the plates are washed 3 times with PBS-Tween buffer, 200 µl in each well.

Buffer Added After Coating: 150 µl of after coating (saline-albumin) buffer is added to each well and incubated 1 hour at room temperature or at 4° C. and stored for up to two months, when the strips are tape-sealed. Immediately prior to the addition of plasma dilutions, the strips are washed three fold with PBS-Tween as above.

Plasma Dilutions: The single standard pooled plasma, which has been prepared to contain 65% (0.65 u/ml) vWf:Ag, or several standards prepared to contain 15% (0.15 u/ml), 35% (0.35 u/ml) as well as 65% (0.65 u/ml) vWf:Ag, are diluted 1:100 in dilution buffer. The normal and abnormal control plasmas and unknown samples are also diluted 1:100. The normal plasma serves as a control to monitor the system. The abnormal control is 0% vWf:Ag.

Addition of Plasma to Strip Wells of a Microtiter Plate:

A. Standard Plasmas: 100 µl of the 15% (0.15 u/ml), 35% (0.35 u/ml) and/or 65% (0.65 u/ml) standard plasma dilutions are added to the first, third, and fifth wells either in series or in replicate strips.

B. Unknown Plasma: 100 µl of the diluted unknown plasma is added to the second, fourth, and sixth wells.

C. Normal and Abnormal Control Plasmas: 100 µl of the normal control is added to the seventh well and 100 µl of the abnormal control is added to the eighth well.

When the plasma dilutions are complete, the plate is sealed with tape and incubated for one hour at room temperature in the dark.

Strip Washing: The plasma dilutions are washed from the wells three times with 200 µl of PBS-Tween.

Addition of Second (Sandwich) Anticanine vWf:Ag:

Following the washing with PBS-Tween, 100 µl of second (e.g. goat) anticanine vWf:Ag appropriately diluted (e.g. 1:250) in dilution buffer is added to each well and the sealing tape is replaced. The strip is incubated for one hour at room temperature in the dark.

Strip Washing: The strips are washed three times with PBS-Tween as above.

Addition of Detector Anti-Immunoglobulin (Anti Sandwich IgG): 100 µl well of peroxidase-conjugated antibody (e.g. porcine anti-goat IgG) appropriately diluted (e.g. 1:10000) in dilution buffer is added. The sealing tape is replaced and the strip is incubated at room temperature for one hour in the dark.

Plate Washing: The plate is washed three times with PBS-Tween as above.

Citrate Buffer Spray: Using an aerosol can the strip is sprayed with citrate buffer three times and is shaken to drain its washings into a sink.

Color Reaction with OPD: Following the spray step, 100 µl of the OPD-H$_2$O$_2$ solution is added to each well. After approximately 10 minutes the reaction is terminated by adding 100 µl well of 4.5M H$_2$SO$_4$.

Unknown Comparisons and Controls: Under standard indoor fluorescent lighting, place the well strips over a white background (3×5 inch card works well) and compare the color intensity of the three wells containing the 65% (0.65 u/ml) vWf:Ag standard or the series of 15% (0.15 u/ml), 35% (0.35 u/ml), and 65% (0.65 u/ml) standards to the unknown samples which are in alternate wells in triplicate. The objective of the comparison is to determine if the unknowns are of more, less, or of equal color intensity than the standards. The normal control plasma is assigned 100% (1 u/ml) vWf:Ag and should be obviously of greater color intensity that the 15%, 35% or 65% standards while the abnormal control .plasma known to be genetically homozygous deficient in vWf has less than 0.002% (0.2 ×10$^{-4}$ u/ml) vWf:Ag and should have no color.

The strip may be read with an ELISA reader at 490 nm with the abnormal control plasma serving as the blank. Comparison of the quantitative optical densities of the triplicate or serial standards and the triplicate unknown sample virtually eliminates any uncertainty of visual comparisons and permits definitive quantitation of the unknown vWf:Ag level.

Interpretation: The color intensity of the unknown is graded as being stronger than, equal to or of lesser color intensity than the standards. Experience with a very large number of such qualitative tests has made it clear that visual comparison readily defines three or more groups of unknown plasma vWf:Ag levels; e.g. below 20% (0.2 u/ml), 30–40% (0.3–0.4 u/ml), 60–75% (0.60–75 u/ml), and greater than 80% (0.8 u/ml).

Using these screening determinations, the clinician or animal breeder can quickly determine if a sample has plasma levels less than or greater than 70–75% (0.7–0.75 u/ml) vWf:Ag. Patients with vWf:Ag levels above 75% are at little or no risk for surgical or other bleeding caused by reduced levels of vWf:Ag or are unlikely to transmit vWd to their offspring.

Plasma from individuals that generate virtually no color reaction are affected with vWD

QUANTITATIVE ELISA PROCEDURE

This procedure utilizes the EL 312 ELISA Plate Reader available from Bio-Tek Instruments, Winooski, VT. However, the procedure is not limited to this specific instrument, as will be evident to those skilled in the art.

Plate Preparation

Microtiter plates with 96 wells (e.g. 96 plate Immulon I, Dynatech Corporation) are coated with 100 µl/well of rabbit anticanine vWf:Ag (the DEAE purified fractions prepared as described above) appropriately diluted (e.g. 1:500) with coating buffer. Fifteen plates are usually coated at once. The plates are stacked and incubated overnight in a humid 37° C. incubator. The top plate is covered by an empty plate. The following day, the plates are washed 3 times with PBS-Tween buffer.

Buffer Added After Coating

200 µl of freshly prepared after-coating buffer is added to each well and incubated 1 hour at room temperature, or at 4° C. for up to two months when the plates are tape-sealed.

Dilution Standards

A pooled plasma from healthy individuals of the species being tested is diluted to create a series of standards [100% (1.0 u/ml), 50% (0.5 u/ml), 25% (0.25 u/ml), 12.5% (0.125 u/ml), and 6.25% (0.0625 u/ml)] to which the unknown sample plasmas will be compared. Six or more tubes are prepared and designated as standards (labelled $STD_1$, $STD_2$, $STD_3$, $STD_4$, and $STD_5$ and a blank is prepared. To the $STD_1$ add 10.0 ml of dilution buffer, to the other standards add 1.0 ml (1000 µl) of dilution buffer. 50 microliters (µl) of the 100% standard is added to 10.0 ml of the dilution buffer in $STD_1$ tube and the tube is capped with Parafilm (3M Corporation) and inverted gently six times—this is a 1:200 dilution. Next, 1000 µl of the 1:200 dilution is added to 1000 µl of dilution buffer in the $STD_2$ tube which equals a 1:400 dilution. With a pipetting device mix the $STD_2$ six times and then add 1000 µl of the mixed $STD_2$ to the $STD_3$ tube and mix as above. Add 1000 µl of the $STD_3$ tube to the $STD_4$ tube and mix; add 1000 µl of $STD_4$ to the $STD_5$ tube and mix. Add 1 ml of dilution buffer to the blank tube.

Dilution of Unknown Samples

One dilution tube for each unknown sample is prepared with buffer before the plasma is pipetted. The tube labeled 1:600 has 12 ml of buffer. The dilution tubes are lined up behind the plasma samples in the test tube rack.

Using a fresh pipette tip for each unknown plasma sample, 20 µl of the plasma sample is added to the 12 ml (1:600 dilution) and capped with fresh Parafilm and inverted six times.

Each unknown plasma sample is similarly diluted. An internal control (reference) plasma of known vWf:Ag level can also be used and diluted similarly. Samples with low and/or no detectable vWf:Ag should also be included on the plate as abnormal controls to assure the specificity, validity, and accuracy of the test.

Addition of Plasma to Wells

Immediately prior to the addition of plasma dilutions to the plates, the wells are washed three times with PBS-Tween, 200 µl/well. 100 µl of each sample is added per well. Dilutions are run in triplicate for each standard. The unknowns are run in triplicate and are distributed on the plate as in the Master Chart shown in Table I. The additions are planned in advance and the Chart is used as a guide. When the plasma additions are complete, the plate is sealed with tape or otherwise covered and stored at 4° C. overnight.

The Master Chart shown in Table I gives the results of an actual test with canine plasma. In the Master Chart, boxes 1–24 are samples to be tested. The boxes marked '83' contain the internal reference plasma having a known value of 83% (0.83 u/ml) vWf:Ag. 'Blk' standard plasma dilutions. The boxes marked "Sple" are the unknown sample plasmas. "AC" is the abnormal control (homozygous vWf:Ag deficient plasma).

Plate Washing

The plasma dilutions are drained from the wells which are then washed three times with PBS-Tween after the overnight step and between each antibody incubation.

Addition of Second (Sandwich) Anticanine vWf:Ag

Following the washing with PBS-Tween, add to each well 100 µl of second (e.g. goat) anticanine vWf:Ag appropriately diluted (e.g. 1:1000) in dilution buffer and replace the sealing tape or cover. Incubate for one hour at room temperature in the dark.

Plate Washing

Three washings with PBS-Tween as above.

Addition of Detector Anti-Immunoglobulin (Anti Sandwich IgG)

Add 100 µl/well of peroxidase-conjugated antibody (e.g. porcine anti-goat IgG) appropriately diluted (e.g. 1:10000) in dilution buffer. Replace the sealing tape or cover and incubate at room temperature for one hour in the dark.

Plate Washing

Three washings with PBS-Tween as above.

Citrate Buffer Spray

Using an aerosol can, spray the plate (6–10 inches away) with citrate buffer three times and vigorously shake the plate's washings into a sink after each spray.

Color Reaction with OPD

Following the spray step, 100 µl of the $OPD-H_2O_2$ substrate is added to each well with a multichannel pipetting device and fresh tips. After approximately 10 minutes, the reaction is terminated by adding 100

μl/well of the 4.5M $H_2SO_4$. The pipette tips do not need to be changed between the OPD and $H_2SO_4$.

Plate Scanning

The top of the plate is wiped dry with a lint-free pad and inserted in an ELISA plate reader and a report form with final results is generated. These results are summarized on the Master Chart (see Table I).

An examination of the chart is convincing of the accuracy of the test as shown by the low deviations in the readings listed in different boxes for the same compositions. Compare, for example $STD_1$ in boxes A-1, A-12 and H-12, or 83 REF in boxes A-7 and H-6.

The optical densities are converted to percent vWf:Ag by comparison with the quadratic curve generated from the triplicate values of the five standards using a soft ware package from the instrument manufacturer.

The Master Chart consolidates all of the above information including sample numbers, machine readings and percent of vWf:Ag per standard, reference or sample.

The specificity, accuracy and reproducibility of the process of this invention will be readily apparent from inspection of the Master Chart.

The wide applicability of the test will be apparent from FIGS. 1 though 11 which are standard curves prepared as described above in which optical density is plotted against the reciprocals of the dilutions for the eleven different species indicated. These curves show that all species cross-react in a linear fashion. These curves could be employed in accordance with the invention to determine the concentration of vWf:Ag in unknown samples from each of the species.

The polyclonal antibodies of this invention, although differing in certain physicochemical properties, have a number of properties in common which contribute to their utility for the practice of the invention. One of the most important of these properties is that in the coating buffer they are sticky and will adhere firmly to a surface useful in the ELISA test. Another is that they form soluble reaction complexes with vWf:Ag from a wide variety of species. Still another is that individually they react with labeled detectant antibodies (anti IgG). For example, goat anti vWf:Ag will react specifically with porcine anti-goat IgG but not with porcine anti-rabbit IgG. Thus in the ELISA test of the invention the detector-IgG reacts with the sandwich antibody, not with the capture antibody, to form a soluble detectable product comprising the capture antibody, the vWf:Ag, the sandwich antibody and the labeled detectant IgG. It is the solubility of the various reactant products formed during the test which makes the invention operable. Polyclonal antibodies to von Willebrand factor raised against species other than canines can also be used in the method of the subject invention, as long as the polyclonal antibodies recognize a conserved epitope. This aspect of the invention is more fully discussed in Example 2.

TABLE I

| | 1 | 2 | 3 | 4 | 5 | 6 | 7 | 8 | 9 | 10 | 11 | 12 |
|---|---|---|---|---|---|---|---|---|---|---|---|---|
| | | | | | | MASTER CHART | | | | | | |
| A | STD 1 | STD 2 | STD 3 | STD 5 | STD 5 | 83 Ref | 83 Ref | BLK | BLK | STD 3 | STD 2 | STD 1 |
| | 1.182 | 0.997 | 0.773 | 0.597 | 0.446 | 0.729 | 0.774 | 0.225 | 0.223 | 0.735 | 0.951 | 1.269 |
| | | | | | | 71% | 80% | | | | | |
| B | Sple 1 | Sple 1 | Sple 1 | Sple 2 | Sple 2 | Sple 2 | Sple 3 | Sple 3 | Sple 3 | Sple 4 | Sple 4 | Sple 4 |
| | 0.869 | 0.862 | 0.785 | 0.767 | 0.758 | 0.549 | 0.572 | 0.561 | 0.614 | 0.642 | 0.663 | |
| | 103% | 101% | 83% | 79% | 77% | 79% | 37% | 41% | 39% | 49% | 54% | 58% |
| C | Sple 5 | Sple 5 | Sple 5 | Sple 6 | Sple 6 | Sple 6 | Sple 7 | Sple 7 | Sple 7 | Sple 8 | Sple 8 | Sple 8 |
| | 0.296 | 0.280 | 0.261 | 0.646 | 0.658 | 0.623 | 0.537 | 0.517 | 0.528 | 0.733 | 0.737 | 0.788 |
| | 0% | 0% | 0% | 55% | 57% | 50% | 35% | 31% | 33% | 72% | 73% | 84% |
| D | Sple 9 | Sple 9 | Sple 9 | Sple 10 | Sple 10 | Sple 10 | Sple 11 | Sple 11 | Sple 11 | Sple 12 | Sple 12 | Sple 12 |
| | 0.845 | 0.745 | 0.706 | 0.248 | 0.269 | 0.264 | 0.705 | 0.687 | 0.706 | 0.635 | 0.648 | 0.731 |
| | 97% | 74% | 66% | 0% | 0% | 0% | 66% | 63% | 66% | 53% | 55% | 71% |
| E | Sple 13 | Sple 13 | Sple 13 | Sple 14 | Sple 14 | Sple 14 | Sple 15 | Sple 15 | Sple 15 | Sple 16 | Sple 16 | Sple 16 |
| | 0.690 | 0.659 | 0.657 | 0.358 | 0.356 | 0.361 | 0.732 | 0.688 | 0.716 | 0.281 | 0.303 | 0.319 |
| | 63% | 57% | 57% | 6% | 5% | 6% | 72% | 63% | 68% | 0% | 0% | 0% |
| F | Sple 17 | Sple 17 | Sple 17 | Sple 18 | Sple 18 | Sple 18 | Sple 19 | Sple 19 | Sple 19 | Sple 20 | Sple 20 | Sple 20 |
| | 0.924 | 0.922 | 0.853 | 0.318 | 0.327 | 0.320 | 0.378 | 0.355 | 0.361 | 0.369 | 0.375 | 0.490 |
| | 117% | 116% | 99% | 0% | 1% | 0% | 9% | 5% | 6% | 7% | 8% | 27% |
| G | Sple 21 | Sple 21 | Sple 21 | Sple 22 | Sple 22 | Sple 22 | Sple 23 | Sple 23 | Sple 23 | Sple 24 | Sple 24 | Sple 24 |
| | 0.972 | 0.927 | 0.902 | 0.843 | 0.836 | 0.840 | 0.616 | 0.584 | 0.549 | 0.627 | 0.614 | 0.666 |
| | 118% | 118% | 111% | 96% | 95% | 96% | 49% | 43% | 37% | 51% | 49% | 58% |
| H | Std 4 | Std 5 | AC | AC | AC | 83 Ref | BLK | STD 5 | STD 4 | STD 3 | STD 2 | STD 1 |
| | 0.688 | 0.499 | 0.231 | 0.214 | 0.241 | 0.768 | 0.251 | 0.484 | 0.624 | 0.783 | 1.001 | 1.071 |
| | | | 0% | 0% | 0% | 79% | | | | | | |

EXAMPLE 2

Use of Multiple Species vWf Antibodies To Detect vWf In Multiple Vertebrate Species The modified double-sandwich ELISA developed for canine von Willebrand factor also cross-reacts with plasma von Willebrand factor of other mammalian species and can be used to quantitate von Willebrand factor in at least 12 other species (see Example 1). Specificity of the assay was demonstrated using vWd plasma from pigs, humans, and a horse. Agarose filtration fractions of cat, rat, and guinea pig plasma when analyzed by ELISA had the reactive antigen in the void volume, which coincided with the typical multimeric pattern for von Willebrand factor. Significant cross-species reactivity was observed between monoclonal antibodies (Mabs) against porcine and bovine von Willebrand factor and plasmas from 12 species. Mixed combinations of Mabs and various polyclonal antibodies to vWf:Ag were used to quantitate vWf:Ag in pig, horse, dog, human, and mouse plasmas. Using Mabs that capture rabbit vWf:Ag and goat antidog vWf:Ag as the sandwich antibody, a quantitative assay for rabbit vWf:Ag was constructed. The same sandwich and conjugate antibody were also used to visualize rabbit von Willebrand factor multimers. These findings permit, for the first time, the measurement of vWf:Ag in a variety of vertebrates for which species-specific immunological reagents are not available.

One embodiment of the subject invention is directed to a modified double-sandwich ELISA for canine vWf:Ag which is cross-reactive with the plasmas of at least 12 other mammalian species and can be used to construct sensitive quantitative assays for vWf:Ag in these species Significant species cross-reactivity was also observed between Mabs and the vWf:Ag of various species. When the Mabs were used in combination with polyclonal antibodies they could also be used to quantitate vWf:Ag.

METHODS

Plasmas—Blood from 14 different mammalian species, including humans and dogs, was collected into 1/10 volume of 3.8% sodium citrate dihydrate and centrifuged twice (18,000 ×g) to render the plasma platelet free. Samples were stored in aliquots at −20° or −40° C. A single plasma sample was obtained from a monkey and manatee, and pooled plasmas (n=6) were prepared from rabbits, rats, guinea pigs, cats, goats, sheep, cows, horses, mice, dogs, pigs, and humans. vWd plasmas from dogs (26), pigs (27), and a horse were used to confirm specificity of the assays. The porcine vWd plasma was kindly supplied by Dr. Walter Bowie of the Mayo Clinic, Rochester, Minn. Human plasmas (BR, DW, SF) were made cell-free, as above, from the citrated blood of laboratory staff. The human blood samples were drawn after informed consent had been obtained under an approved protocol from the Institutional Review Board of the New York State Department of Health and according to the Principles of the Declaration of Helsinki. The vWf:Ag-depleted human plasma (AC) was purchased from BioData Corp. (Horsham, Pa.).

Agarose Filtration—Ten ml of pooled plasma from laboratory rats, guinea pigs, rabbits, or domestic short-haired cats was filtered at room temperature with phosphate-buffered saline, pH 7.4, at 20 ml per hour over a 2.5×45-cm 6% agarose (Bio-Gel A5M, Bio-Rad, Rockville Centre, N.Y.) column. The absorbance of the 5-ml fractions was monitored at 280 nm. As collected, each fraction was stored at 4.C and after completion of the chromatography, was divided into 0.5-ml aliquots and stored at −50° C. The fractions were subsequently assayed for vWf:Ag and for the presence of von Willebrand factor multimers as previously described (28).

Antibodies—Antibodies to canine vWf:Ag were prepared in a rabbit and a goat (29). The immune sera were adsorbed twice (30) with cryoprecipitate from the plasma of a dog homozygous for type III vWd (see Example 1). IgG was prepared (31) from the goat and rabbit sera and was stored at −50° C. The same purified vWf:Ag preparation used to immunize the goat was used to immunize four Balb/C mice (32). Pre-fusion mouse serum samples were pooled and used as a sandwich antibody. Six ascitic-fluid Mabs against bovine vWf:Ag (No.'s 1,2,6,7,16&10) were kindly supplied by Dr. Edward Kirby of Temple University, Philadelphia, Pa. (25,33). Seven Mabs against porcine vWf:Ag were kindly supplied by Dr. David Fass of the Mayo Clinic, Rochester, MN and were in IgG form (W1-1, W1-2, W1-5) or ascitic fluid (W1-3, W1-4, W1-8, W1-16) (22,34). Rabbit antiporcine vWf:Ag (11) was supplied by Dr. Bowie. Commercially purchased antibodies were rabbit antihuman vWf:Ag supplied by DAKO, Carpenteria, Calif., and pig anti-goat IgG conjugated to horseradish peroxidase, goat anti-mouse IgG-horseradish peroxidase and goat anti-rabbit IgG-horseradish peroxidase, each supplied by TAGO, Inc., Burlingame, Calif..

Reagents—Coating buffer: 0.05M sodium carbonate, pH 9.6. Blocking buffer: 0.9% NaCl, 0.2% bovine serum albumin (Sigma, St. Louis, MO, #6793) in 0.003M tris, pH 7.4. Dilution buffer: 0.9% NaCl, 0.05% bovine serum albumin, 0.003M Na ethylenediamine tetracetic acid, 0.02M tris, pH 7.4. Citrate buffer: 0.033M $C_6H_8O_7$, 0.067M $Na_2HPO_4$, pH 5.0. Washing buffer: phosphate-buffered saline, 0.5% V/V Tween-20, pH 7.4. All of the above buffers contained 0.1 mg% thimerosal. Horseradish peroxidase indicator substrate: 30 mg tablet o-phenylenediamine dihydrochloride (Sigma #P8412) dissolved in 33 ml of citrate buffer plus 150 μl of 3% $H_2O_2$.

Microtiter plate coating—Immulon I microtiter plates (Dynatech, Alexandria, Va.) were coated with various antibodies by dilution in the coating buffer and dispensing 100 μl of the solution into each well of the microtiter plate, covering the plate and incubating it overnight in a moist 37° C. chamber. The following morning the wells were flushed three times with washing buffer, and 200 μl of blocking buffer was stored in the wells (at least overnight) at 4° C. until the plate was used. Plates stored at 4° C. with blocking buffer were reactive for at least three months. Plates were coated with the rabbit antidog vWf:Ag IgG at a 1:500 dilution or rabbit antihuman vWf:Ag IgG at a 1:4000 dilution or rabbit antiporcine vWf:Ag at 1:1000 dilution. The antiporcine and antibovine vWf:Ag Mabs were utilized as coating antibodies at a 1:100 dilution.

ELISA—Coated plates were flushed with 100 μl of washing buffer three times and then 100 μl of the appropriate dilution of plasma was loaded into the wells and incubated for one hour at room temperature. The plates were flushed as above and 100 μl of the diluted sandwich antibody was added to the wells, incubated for one hour and flushed. 100 μl of the conjugated antibody diluted 1:10,000 was added to each well for an additional one hour incubation. Following a final PBS-Tween wash, conjugated antibodies were sprayed with citrate buffer three times before the addition of the o-phenylenediamine dihydrochloride substrate. The substrate color change was halted after 5–20 minutes with $H_2SO_4$. Plates were scanned at 490 nm with a Bio-Tek EL312 microplate reader (Bio-Tek, Winooski, Vt.). Standard curves were constructed and sample concentrations were determined with the BIO-TEK Kinicalc software program, which plotted the logarithm of the optical density versus the logarithm of the concentration and employed a quadratic curve fit.

RESULTS

When an antibody combination of rabbit antidog vWf:Ag as capture reagent and goat antidog vWf:Ag as sandwich antibody, at 1:10 and 1:100 dilutions was used, plasmas from 10 species studied exhibited moderate to strong reactivity. Cow and mouse plasmas showed weaker reactions, which were substantially above the blanks. Rabbit plasma was unreactive using this antibody configuration. When the sandwich antibody concentration was decreased to 1:1000, the dog, cat, sheep and goat plasmas continued to strongly react. Human plasma also strongly reacted in this ELISA. The absorbance data in Table II demonstrate the relative cross-reactivities of various animal plasmas using polyclodal capture and sandwich antibodies to canine von Willebrand factor.

The absorbances of type III vWd plasmas from pigs and dogs, and vWf:Ag-depleted human plasma at the 1:100 dilution did not generate absorbances above the buffer blank in this ELISA. When type I vWd plasmas of pigs and humans were quantitated in the canine-specific ELISA, the vWf:Ag levels were comparable to the results of ELISAs with species-specific antibodies (Table III).

Figure 12:
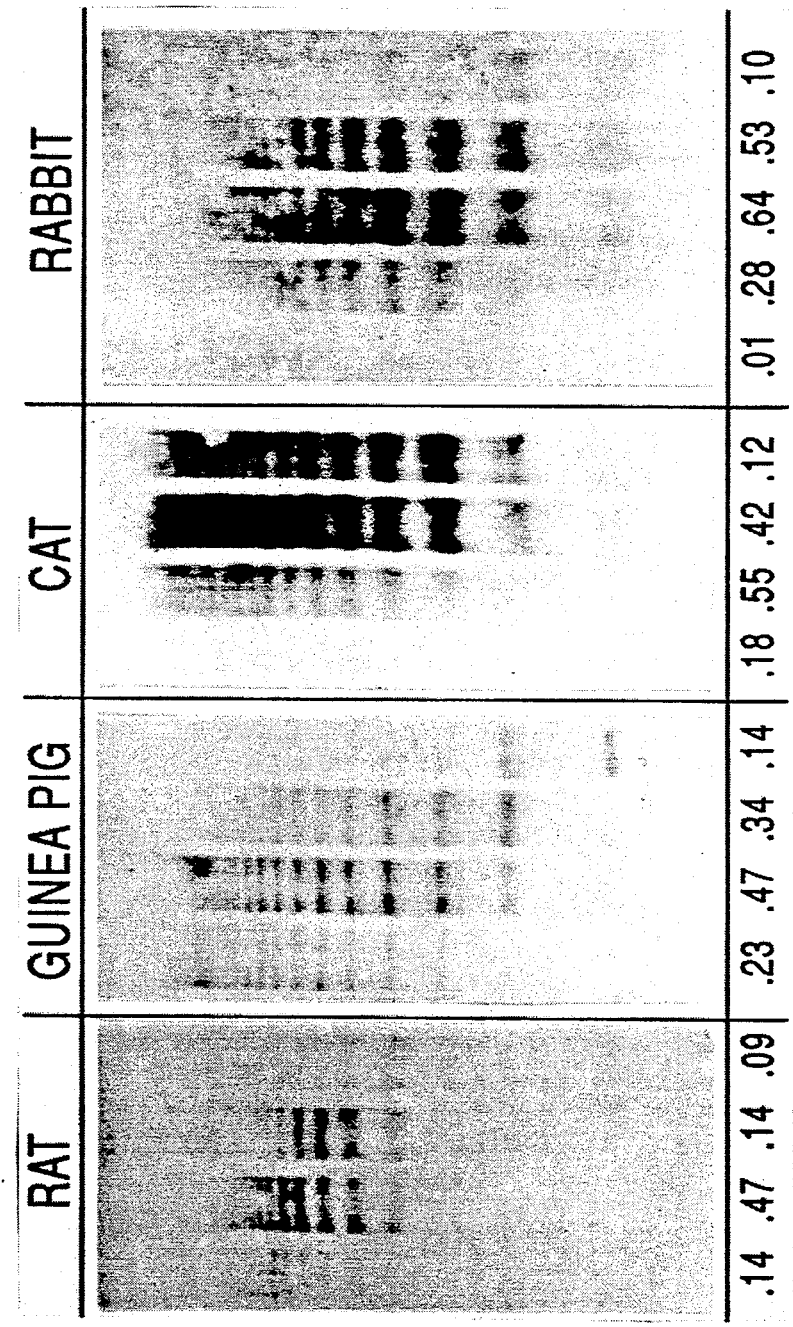
FIG. 12 illustrates the detection of purified von Willebrand factor by ELISA. The fractions are separations of von Willebrand factor multimers by sodium dodecyl sulfate-agarose (1.4%) electrophoresis followed by electroblotting onto nitrocellulose and immuno-localization and visualization with anti-von Willebrand factor and peroxidase-conjugated antibody.

When cat, guinea pig, and rat plasmas were fractionated on a 6% agarose column, the canine-specific ELISA readily detected an antigen in the $V_o$ that coincided with a multimeric protein pattern typical of vWf:Ag. The multimer patterns and antigen detected by the canine-specific ELISA are shown in FIG. 12.

Using pooled polyclonal mouse antidog vWf:Ag as an alternative sandwich antibody at a 1:100 dilution, dose-response curves were constructed for 11 of the survey plasmas at doubling dilutions from 1:25 to 1:1600. The relative cross-reactivity for vWf:Ag for this antibody system is shown in Table IV. Quantitation of vWf:Ag in vWd pig and human plasmas using this mouse sandwich antibody paralleled those shown in Table III for goat antidog vWf:Ag sandwich antibody.

Studies that employed 13 different Mabs prepared against porcine and bovine vWf:Ag as the capture reagent and goat antidog vWf:Ag as the sandwich antibody demonstrated that the plasmas of the 12 survey species reacted positively (greater than three times the average blank) in 54 of the 156 possible antibody combinations. The antibovine Mab #10/goat antidog system reacted positively with plasmas of six species while the antiporcine Mab W1-5/goat antidog combination cross-reacted positively with plasmas of lo of the 12 species tested. The reactivities of these 12 plasmas with each Mab/goat antidog combination is reported in Table V.

The very strong reaction of rabbit plasma with the anti-porcine Mabs W1-1, W1-2, W1-5 was further investigated by partially purifying rabbit von Willebrand factor by filtering 10 ml of pooled rabbit plasma over an agarose column as above and testing the with each Mab/goat antidog combination. The factor VIII coagulant activity of the fractions was measured (15) and found in the $V_o$ fractions. Each of the above porcine Mabs reacted with the rabbit plasma and the $V_o$ fractions. Construction of a rabbit plasma standard curve permitted the quantitation of the $V_o$ reactive antigen, which is reported in FIG. 12. Using the W1-5/goat antidog antibody combination, recovery of the reactive antigen was 76.9%. Sodium dodecyl sulfate agarose-gel electrophoresis and immunoblotting of the rabbit plasma agarose filtration fractions utilizing the same sandwich and conjugate antibodies as in the above ELISA demonstrated the presence of high-, intermediate-, and low-molecular-weight multimers in rabbit plasma as well as their presence in the various fractions (FIG. 12).

When the order of applying antiporcine and antibovine Mabs was reversed and they were used as sandwich antibodies, with rabbit antidog vWf:Ag serving as the capture reagent, the pattern of reactivities changed, as shown in Table VI. Antibovine Mab #10 and antiprocine Mab W1-5 still generated the highest percentage of cross reactivities; 10 of the 13 Mabs now reacted positively against their respective homologous antigens. However no reactivity with rabbit plasma was observed when the Mabs and rabbit anticanine vWf:Ag were in the sandwich and capture configuration, respectively.

Using rabbit antihuman vWf:Ag as the capture antibody and antibovine Mab #16 as the sandwich antibody, canine and porcine plasma vWf:Ag was quantitated in five samples from each species. The vWf:Ag levels of these plasma samples were also determined by porcine or canine specific ELISAs. The results of these assays are reported in Table III and demonstrate that the vWf:Ag levels measured in the mixed antibody systems were parallel to the ELISA using species-specific antibodies.

DISCUSSION

Using antibodies specific for canine vWf:Ag, applicants found that numerous other mammalian plasmas were reactive in this system (see Example 1). The detected antigen from cat, rat, and guinea pig plasma eluted in the $V_o$ from agarose filtrations, suggesting that the reactive protein in these plasmas was von Willebrand factor. Specificity for the von Willebrand factor protein was confirmed by the fact that type III canine and porcine vWd and human von Willebrand factor-depleted plasmas are nonreactive. Porcine and human type I vWd plasmas demonstrated parallel reductions of vWf:Ag when assayed in the canine system or in their homologous antibody systems. Collectively these data indicated that the canine-specific ELISA detects the vWf:Ag of many other species. This ELISA antibody system was used in combination with other diagnostic assays to confirm, for the first time, type III vWd in the horse.

With the canine ELISA described in Example applicants were able to also construct dose-response curves for 11 survey plasmas in which the lower limit of detection is at least $1.5 \times 10^{-3}$ un/ml for each species (see FIGS. 1-11). These data demonstrate the potential of quantitating vWf:Ag in each of these species without the need for species-specific antibodies. This assay can be especially useful for small laboratory animals such as guinea pigs, rats, and mice for which it is difficult to prepare sufficient quantities of immunogen, or for rare or wild species in which plasma is not readily available for immunogen preparation. Using this technique, applicants have developed a quantitative ELISA for mouse vWf:Ag and have recently identified hypothyroid mice with reduced levels of plasma vWf:Ag.

Species cross-reactivities in the ELISA were further evaluated by utilizing 13 different Mabs prepared against either bovine or porcine vWf:Ag as probes or capture antibodies. The data presented in Tables V and VI demonstrate both the species-related differences in reactivity as well as reactive epitope conservation across species lines. Furthermore, these results clearly indicate that cross-reactivity is not exclusive to the canine polyclonal antibody system.

For those species reactive with a single but not other Mabs it is clear that the capture antibody was the nonreactive component in the antibody-antigen-antibody combination. The observation that cow and mouse plasma were unreactive in each of the 13 Mab capture systems may not reflect a lack of reaction with the capture antibodies, but rather a weak interaction with the sandwich antibody. Cow and mouse plasma also appeared unreactive in the canine polyclonal system, when the same concentration of goat antibody was used as sandwich antibody.

A parallel response pattern for dog and cat plasmas was observed with each of the six antibovine Mabs, which suggested similar immunologic regions for the vWf:Ag of these two species. This is reinforced by the observation that the vWf:Ag of cat plasma is one of the few heterologous vWf:Ags readily measured in the Laurell electro-immunoassay system using rabbit anticanine vWf:Ag (20).

In solid phase/capture antibody configuration, antiporcine Mabs W1-4, W1-8, and W1-16 were highly species-specific and exhibited little interspecies reactions. In contrast antiporcine Mabs W1-1, W1-2, and W1-5 each showed considerable and similar cross reactivity, exhibiting positive interactions with guinea pig, horse, monkey, sheep, pig, dog, goat and rabbit plasmas. The parallel reactivities for cat and dog vWf:Ag were again observed, however the W1-2 Mab captures canine, but not feline vWf:Ag.

Of interest was the finding that W1-1, W1-2, and 1-5 Mabs each reacted with a rabbit plasma antigen, then reacted with goat antidog vWf:Ag in liquid phase. The three antiporcine Mabs also reacted with partially purified rabbit von Willebrand factor.

The goat antidog reactivity with the rabbit $V_o$ protein suggested that this antibody could be used to identify rabbit vWf multimers. Sodium dodecyl sulfate-electrophoresis and electroblotting of rabbit plasma and agarose $V_o$ fractions demonstrated the typical vWf:Ag multimer patterns for the samples. These findings confirm that the above ELISA antibody system was detecting rabbit vWf:Ag. When used in combination with multimer electrophoresis these techniques provide sensitive qualitative and quantitative methods for the analysis of rabbit von Willebrand factor.

When the Mabs to bovine and porcine vWf:Ag were used in the reverse configuration as sandwich instead of capture antibodies, five of six anti-bovine Mabs now reacted positively with cow plasma and suggested that the lack of reaction in the capture configuration may have been caused either by a weakly reacting sandwich antibody or by the solid/liquid phase differences that exist for some Mabs against vWf:Ag (22). The most striking example of this difference is antiporcine Mab W1-4, which is nonreactive with pig plasma in the solid/capture phase, but has the highest affinity of the seven antiporcine Mabs with pig plasma when used in the liquid/sandwich phase.

Using five different antihuman Mabs against vWf, Hornsey reported that in a liquid phase assay the sera of ox, pig, dog, rabbit, sheep, chicken, donkey, goat, and rat were all unreactive, while human sera showed full cross-reactivity (35). In a limited study, matched plasma and serum samples from a dog, human, and pig with normal plasma vWf:Ag levels were compared in three different ELISAs using antibodies specific for each species vWf. Applicants found that the three plasmas were strongly reactive in each ELISA antibody system, however the three serum samples were unreactive with either the homologous or heterologous antibody configurations.

Preliminary data suggested that polyclonal antibodies prepared in rabbits, goats, and mice to canine vWf:Ag will react with their homologous vWf:Ag (i.e. goat antidog vWf:Ag reacting with goat vWf:Ag) if the antibodies are used in liquid, but not solid phase. This was tested by using the rabbit, goat, or mouse anticanine vWf reagents as either capture or sandwich antibodies. In each case the homologous vWf:Ag reacted strongly with its respective antibody in the liquid but not solid phase.

A mixed antibody system of rabbit antihuman vWf:Ag as capture antibody and antibovine Mab #16 as sandwich antibody was used to measure canine and porcine vWf:Ag. The parallel results for the canine- and porcine-specific assays demonstrated the potential for developing quantitative ELISAs using species-heterologous systems. The lower limit of vWf:Ag detection in the four mixed ELISA systems reported was at least $1.5 \times 10^{-3}$ un/ml.

TABLE II

ELISA Cross-reactivities of mammalian plasmas using antibodies specific for canine von Willebrand factor. Plasmas were diluted 1:100 (A) and 1:1000 (B).

| | ABSORBANCE AT 490 nm Sandwich Antibody Dilution | | | | | |
|---|---|---|---|---|---|---|
| | 1:10 | | 1:100 | | 1:1000 | |
| SPECIES | A | B | A | B | A | B |
| Guinea Pig | 1.775 | 0.976 | 1.189 | 0.419 | 0.480 | 0.207 |
| Dog | >4.000 | 1.212 | 2.829 | 0.683 | 1.610 | 0.486 |
| Cow | 1.123 | 0.967 | 0.308 | 0.305 | 0.155 | 0.145 |
| Horse | 1.944 | 0.961 | 1.000 | 0.435 | 0.279 | 0.133 |
| Cat | 2.916 | 1.310 | 2.455 | 0.803 | 1.136 | 0.345 |
| Monkey | 2.242 | 1.155 | 1.552 | 0.563 | 0.512 | 0.209 |
| Sheep | 1.571 | 0.748 | 0.898 | 0.350 | 0.903 | 0.230 |
| Pig | 2.089 | 1.072 | 1.277 | 0.470 | 0.362 | 0.180 |
| Rat | 1.046 | 0.738 | 0.765 | 0.379 | 0.290 | 0.157 |
| Goat | 1.577 | 0.670 | 1.219 | 0.396 | 1.265 | 0.280 |
| Mouse | 0.811 | 0.605 | 0.430 | 0.231 | 0.214 | 0.136 |
| Manatee | 1.061 | 0.414 | 0.799 | 0.300 | 0.300 | 0.159 |

TABLE III

Human, porcine, and canine plasma vWF:Ag levels (%) determined by ELISA in specific and mixed antibody systems.

| | Capture Antibody | | | |
|---|---|---|---|---|
| | Rabbit AD | Rabbit AH | Rabbit AP | Rabbit AH |
| | Sandwich Antibody | | | |
| SAMPLE | Goat AD | Goat AH | APM/W1-4 | AMB/#16 |
| human-BR | 95 | 89 | — | — |
| human-DW | 51 | 39 | — | — |
| human-SF | 64 | 57 | — | — |
| human-CA | 0.00 | 0.00 | — | — |
| pig-2330 | 30 | — | 30 | 34 |
| pig-2340 | 19 | — | 24 | 38 |
| pig-2385 | 24 | — | 25 | 33 |
| pig-2389 | 15 | — | 24 | 31 |
| pig-2353 | 0.00 | — | 0.08 | 0.13 |
| dog-1130.7 | 51 | — | — | 49 |
| dog-1131 | 61 | — | — | 58 |
| dog-1133 | 27 | — | — | 31 |
| dog-1136.5 | 3.3 | — | — | 2.7 |
| dog-SC | 0.00 | — | — | 0.00 |

AD - antidog vWF,
AH - antihuman vWF,
AP - antipig vWF,
APM - antipig Mab,
ABM - antibovine Mab

TABLE IV

ELISA cross-reactivities of mammalian plasmas by ELISA using rabbit (capture) and mouse (sandwich) antibodies specific for canine von Willebrand factor.

| | ABSORBANCE AT 490 nm | | | | | | | | OPD REACTION TIME |
|---|---|---|---|---|---|---|---|---|---|
| | PLASMA DILUTION | | | | | | | | |
| Species | 1:25 | 1:50 | 1:100 | 1:200 | 1:400 | 1:800 | 1:1600 | BLANK | |
| Guinea Pig | 0.792 | 0.685 | 0.494 | 0.374 | 0.329 | 0.286 | 0.236 | 0.206 | 15 min |
| Cow | 1.027 | 0.739 | 0.526 | 0.360 | 0.269 | 0.264 | 0.211 | 0.203 | 13 |
| Horse | 1.022 | 0.780 | 0.596 | 0.481 | 0.227 | 0.251 | 0.226 | 0.193 | 12 |
| Cat | 0.879 | 0.640 | 0.560 | 0.400 | 0.262 | 0.260 | 0.161 | 0.114 | 6 |
| Monkey | 0.969 | 0.852 | 0.700 | 0.464 | 0.272 | 0.217 | 0.220 | 0.161 | 11 |
| Sheep | 0.889 | 0.790 | 0.678 | 0.550 | 0.293 | 0.206 | 0.197 | 0.134 | 8 |
| Pig | 0.887 | 0.737 | 0.604 | 0.470 | 0.364 | 0.305 | 0.230 | 0.144 | 8 |
| Rat | 0.718 | 0.587 | 0.462 | 0.383 | 0.340 | 0.277 | 0.525 | 0.231 | 20 |
| Dog | 1.099 | 0.924 | 0.788 | 0.630 | 0.450 | 0.340 | 0.210 | 0.120 | 5 |
| Mouse | 0.804 | 0.620 | 0.433 | 0.347 | 0.294 | 0.262 | 0.253 | 0.257 | 20 |
| Goat | 0.992 | 0.866 | 0.688 | 0.432 | 0.230 | 0.259 | 0.232 | 0.164 | 10 |
| Rabbit | 0.230 | 0.206 | 0.234 | 0.234 | 0.222 | 0.198 | 0.222 | 0.225 | 20 |

OPD - o-phenylenediamine dihydrochloride

TABLE V

Cross-reactivities of mammalian plasmas in an vWF:Ag ELISA using Mabs as the capture antibody and goat antidog vWF:Ag as the sandwich antibody.

| CAPTURE ANTIBODY: | G. Pig | Cow | Horse | Cat | Monkey | Sheep | Pig | Rat | Dog | Mouse | Goat | Rabbit |
|---|---|---|---|---|---|---|---|---|---|---|---|---|
| | | | | | Ratio of Absorbance to Blank | | | | | | | |
| Antibovine Mabs | | | | | | | | | | | | |
| 1-AF (3/16/83) | 2 | 2 | 3 | 10 | 2 | 4 | 2 | 2 | 8 | 2 | 3 | 5 |
| 2-AF (5/31/83) | 1 | 2 | 1 | 1 | 1 | 3 | 2 | 2 | 2 | 2 | 4 | 8 |
| 6-AF (4/16/87) | 1 | 2 | 5 | 9 | 2 | 4 | 2 | 1 | 10 | 1 | 3 | 4 |
| 7-AF (5/31/83) | 1 | 1 | 5 | 10 | 1 | 3 | 1 | 1 | 9 | 1 | 2 | 4 |
| 16-AF (1/14/83) | 2 | 1 | 1 | 3 | 1 | 2 | 2 | 1 | 4 | 1 | 2 | 1 |
| 10-AS (4/16/87) | 7 | 2 | 2 | 12 | 1 | 5 | 10 | 2 | 11 | 2 | 4 | 3 |
| Antiporcine Mabs | | | | | | | | | | | | |
| W1-3-AF | 3 | 1 | 1 | 17 | 13 | 2 | 10 | 1 | 16 | 1 | 2 | 3 |
| W1-4-AF | 1 | 1 | 1 | 1 | 1 | 1 | 1 | 1 | 1 | 1 | 1 | 6 |
| W1-8-AF | 1 | 1 | 1 | 1 | 1 | 2 | 5 | 1 | 1 | 1 | 1 | 1 |
| W1-16-AF | 1 | 1 | 1 | 1 | 1 | 2 | 11 | 1 | 1 | 1 | 1 | 1 |
| W1-1-IgG | 7 | 2 | 12 | 2 | 17 | 9 | 13 | 1 | 1 | 2 | 4 | 14 |
| W1-2-IgG | 7 | 2 | 7 | 2 | 11 | 11 | 9 | 3 | 13 | 2 | 4 | 12 |
| W1-5-IgG | 8 | 1 | 6 | 11 | 4 | 5 | 7 | 7 | 17 | 3 | 6 | 13 |

AF - Ascitic fluid,
IgG - IgG fraction of AF,
AS - (NH$_4$)$_2$SO$_4$ fraction of AF

TABLE VI

Cross-reactivities of mammalian plasmas in an vWF:Ag ELISA using rabbit antidog vWF:Ag as the capture antibody and Mabs against bovine or porcine vWF:Ag as the sandwich antibody.

| SANDWICH ANTIBODY: | G. Pig | Cow | Horse | Cat | Monkey | Sheep | Pig | Rat | Dog | Mouse | Goat | Rabbit |
|---|---|---|---|---|---|---|---|---|---|---|---|---|
| | | | | | Ratio of Absorbance to Blank | | | | | | | |
| Antibovine Mabs | | | | | | | | | | | | |
| 1-AF (3/16/83) | 2 | 4 | 2 | 3 | 2 | 4 | 2 | 2 | 2 | 2 | 3 | 2 |
| 2-AF (5/31/83) | 2 | 4 | 2 | 2 | 2 | 3 | 2 | 2 | 2 | 2 | 3 | 2 |
| 6-AF (4/16/87) | 2 | 4 | 2 | 3 | 2 | 4 | 2 | 2 | 2 | 2 | 3 | 2 |
| 7-AF (5/31/83) | 2 | 4 | 2 | 3 | 2 | 4 | 2 | 2 | 3 | 2 | 4 | 2 |
| 16-AF (1/14/83) | 3 | 3 | 2 | 5 | 2 | 4 | 4 | 2 | 7 | 2 | 4 | 2 |
| 10-AS (4/16/87) | 3 | 6 | 3 | 6 | 3 | 6 | 4 | 3 | 7 | 3 | 6 | 3 |
| Antiporcine Mabs | | | | | | | | | | | | |
| W1-3-AF | 3 | 2 | 2 | 4 | 3 | 3 | 3 | 2 | 3 | 2 | 3 | 2 |
| W1-4-AF | 3 | 3 | 3 | 7 | 7 | 3 | 8 | 3 | 2 | 3 | 3 | 3 |
| W1-8-AF | 3 | 3 | 3 | 3 | 3 | 3 | 4 | 3 | 3 | 3 | 3 | 3 |
| W1-16-AF | 2 | 2 | 2 | 2 | 2 | 2 | 5 | 2 | 2 | 2 | 2 | 2 |
| W1-1-IgG | 3 | 2 | 3 | 2 | 2 | 2 | 3 | 2 | 2 | 2 | 2 | 2 |
| W1-2-IgG | 2 | 2 | 2 | 2 | 2 | 2 | 3 | 4 | 2 | 3 | 2 | 2 |
| W1-5-IgG | 3 | 3 | 4 | 4 | 2 | 4 | 4 | 2 | 6 | 2 | 4 | 2 |

AF - Ascitic fluid,
IgG - IgG fraction of AF,
AS - (NH$_4$)$_2$SO$_4$ fraction of AF

REFERENCES

1. Zimmerman, T. S., Ratnoff, O. D., and Powell, A. E., J Clin Invest 50: 244-254 (1971).
2. Sakariassen, K. S., Bolhius, P. A., and Sixma, J. J., Nature 279: 636-8 (1979).
3. Hoyer, L. W., Blood 58: 1-13 (1981).

4. Tuddenham, E. G. D., Blood Reviews 251-262 (1989).
5. Fass, D. N., Brockway, W. J., Owen, C. A. Jr., and Bowie, E. J. W., Thromb Res 8: 319-327 (1976).
6. Benson, R. E. and Dodds, W. J., Blood 48: 521-9 (1976).
7. Griggs, T. R., Potter, J., McClanahan, S. B., Webster, W. P., and Brinkhous, K. M., Proc Natl Acad Sci USA 74: 759-763 (1977).
8. Kindgon, H. S. and Hassell, T. M., Blood 58: 868-872 (1981).
9. Benson, R. E., Bouma, B. N., and Dodds, W. J., Thromb Res 7: 383-9 (1975).
10. Slappendel, R. L., Tijdschrift Voor Diergeneeskunde 100: 1075-1088 (1975).
11. Olson, J. D., Brockway, W. J., Fass, D. N., Bowie, E. J. W., and Mann, K. G., J Lab Clin Med 89: 1278-1294 (1977).
12. Clowes, A. W., Collazzo, R. E., and Karnovsky, M. J., Lab Invest 39: 141-150 (1978).
13. Nachman, R., Levine, R., and Jaffe, E. A., J Clin Invest 60: 914-921 (1977).
14. Schmer, G., Kirby, E. P., Teller, D. C., and Davie, E. W., J Biol Chem 247: 2512-2521 (1972).
15. Benson, R. E. and Dodds, W. J., Br J Haematol 31: 437-447 (1975).
16. Turitto, V. T., Weiss, H. J., Zimmerman, T. S., and Sussman, I. I., Blood 65: 823-831 (1985).
17. Bennett, B. and Ratnoff, W. D., Proc Soc Exp Biol Med 143: 701-6 (1973).
18. Coppola, R., Lombardi, R., Hawkey, C., Ruggeri, Z. M., and Mannucci, P. M., Thromb Res 17: 473-480 (1980).
19. Bouma, B. N., Dodds, W. J., van Mourik, J. A., Sixma, J. J., and Webster, W. P., Scan J Haematol 17: 263-275 (1976).
20. Cotter, S. M., Brenner, R. M., and Dodds, W. J., J Am Vet Med Assoc 172: 166-8 (1978).
21. Johnson, G. S., Turrentine, M. A., and Sculley, P. W., Thromb Res 42: 419-423 (1986).
22. Katzman, J. A., Mujwid, D. K., Miller, R. S., and Fass, D. N., Blood 58: 530-6 (1981).
23. Bradley, L. A., Franco, E. L., and Reisner, H. M., Clin Chem 30: 87-92 (1984).
24. Meyer, D., Zimmerman, T. S., Obert, B., and Edgington, T. S., Brit J Haematol 57: 597-608 (1984).
25. Mascelli, M. A., Edgington, T. S., and Kirby, E. P., Biochem 25: 6325-6335 (1986).
26. Jolly, R. D., Dodds, W. J., Ruth, G. R., and Trauner, D. B., in Advances in Veterinary Science and Comparative Medicine, Cornelius, C. F. and Simpson, C. F., Eds., Academic Press, New York, pp. 245-276 (1984).
27. Fass, D. N., Bowie, E. J. W., Owen, C. A., and Zollman, P. E., Blood 53: 712-9 (1979).
28. Brosstad, F., Kjanniksen, I., Ronning, B., and Stromorken, H., Thromb Haemost 55: 276-8 (1986).
29. Benson, R. E., Jones, D. W., and Dodds, W. J., Vet Immunol Immunopath 7: 337-346 (1984).
30. Benson, R. E. and Dodds, W. J., Vet Immunol Immunopath : 21-30 (19 6).
31. Goding, J. W., in Monoclonal Antibodies: Principles and Practice, Academic Press, London, pp. 108-121 (1986).
32. Goodall, A. H., Jarvis, J., and Chand, S. et al., Brit J Haematol 59: 565-577 (1985).
33. Mascelli, M. A. and Kirby, E. P., Biochem 27: 1274-1284 (1988).
34. Bowie, E. J. W., Fass, D. N., and Katzmann, J. A., Blood 62: 146-151 (1983).
35. Hornsey, V., Micklen, L. R., and McCann, M. C. et al., Thrombosis and Haemostasis 54: 510-514 (1985).
36. Silveira et al., Thrombosis Research 43: 91-102 (1986).
37. CDC—Guidelines for prevention of transmission of human immunodeficiency virus and hepatitis B virus to healthcare and public safety workers, MMWR 38(S-6): 1-37 (June 23, 1989).
38. Peake, I. R. and Bloom, A. L., Thrombosis Research 10: 27-32 (1977).
39. Benson, R. E., Jones, D. W., and Dodds, W. J., Am J Vet Res 44: 399-403 (1983).
40. Zimmerman, T. S., Hoyer, L. W., Dickson, L., and Edgington, T. S., J Lab Clin Med 86: 152-159 (1975).
41. Kohler, G. and Milstein, C., Nature 256: 495-497 (1975).

What is claimed is:

1. An antibody directed to von Willebrand factor antigen characterized by being capable of factor antigen, the epitope being evolutionarily conserved among vertebrate species.

2. The antibody of claim 1, wherein the vertebrate species is warm-blooded.

3. The antibody of claim 2, wherein the warm-blooded vertebrate species is selected from the group consisting of human, canine, porcine, bovine, guinea pig, horse, cat, monkey, sheep, rat, mouse, goat, rabbit, manatee, llama, and camel.

4. The antibody of claim 1, wherein the antibody is a polyclonal antibody.

5. The polyclonal antibody of claim 4, wherein the polyclonal antibody is raised in a vertebrate species and is purified by adsorption with plasma substantially free of von Willebrand factor antigen.

6. The polyclonal antibody of claim 5, wherein the vertebrate species in which the polyclonal antibody is raised is a rabbit.

7. The polyclonal antibody of claim 5, wherein the vertebrate species in which the polyclonal antibody is raised is a goat.

8. The antibody of claim 1, wherein the antibody is a monoclonal antibody.

9. The antibody of claim 1, wherein the antibody is labeled with a detectable marker.

10. The antibody of claim 9, wherein the detectable marker is an enzyme.

11. The antibody of claim 10, wherein the enzyme is horseradish peroxidase.

12. The antibody of claim 10, wherein the enzyme is alkaline phosphatase.

13. The antibody of claim 1, wherein the epitope is necessary for functioning of the von Willebrand factor.

14. A method of detecting von Willebrand factor antigen in a sample from a vertebrate species which comprises (a) contacting the sample with the antibody of claim 9 such that the von Willebrand factor antigen binds to the antibody and forms a complex therewith, and (b) detecting the antibody present in such complex, thus detecting the von Willebrand factor antigen.

15. A method of detecting von Willebrand factor antigen in a sample from a vertebrate species which comprises:

(A) contacting the sample with the antibody of claim 1 such that the von Willebrand factor antigen binds to the antibody and forms a complex therewith;

(B) contacting the complex formed in step (A) with a second antibody of claim 1 labeled with a detectable marker, so as to form a second complex which includes the antibody of step (A), the von Willebrand factor antigen, and the second antibody; and (C) detecting the second antibody present in the second complex formed in step (B), thus detecting the von Willebrand factor antigen.

16. A method of detecting von Willebrand factor antigen in a sample from a vertebrate species which comprises:

(A) contacting the sample with the antibody of claim 1 such that the von Willebrand factor antigen binds to the antibody and forms a complex therewith;

(B) contacting the complex formed in step (A) with a second antibody of claim 1, so as to form a second complex which includes the antibody of step (A), the von Willebrand factor antigen, and the second antibody;

(C) contacting the second complex formed in step (B) with a third antibody directed to the second antibody of step (B) labeled with a detectable marker, so as to form a third complex which includes the antibody of step (A), the von Willebrand factor antigen, the second antibody of step (B), and the third antibody; and (D) detecting the third antibody present in the third complex formed in step (C), thus detecting the von Willebrand factor antigen.

17. The method of claim 15 or 16 wherein the antibody in step (A) is attached to an immunological reaction surface.

18. The method of claim 17, wherein the immunological reaction surface is a test tube, a well, a bead, a rod, or a strip.

19. The method of claim 18, wherein the immunological reaction surface is glass, plastic, or paper.

20. The method of claim 19, wherein the plastic is polystyrene or polyacrylate.

21. The method of claim 14, wherein the sample is insolubilized to a matrix.

22. The method of claim 21, wherein the matrix is charged nylon or nitrocellulose.

23. The method of claim 14, 15 or 16, wherein the detectable marker is an enzyme.

24. The method of claim 23, wherein the enzyme is horseradish peroxidase.

25. The method of claim 23, wherein the enzyme is alkaline phosphatase.

26. The method of claim 14, 15 or 16, wherein the sample comprises a biological fluid.

27. The method of claim 26, wherein the biological fluid comprises serum or plasma.

28. The method of claim 27, wherein the biological fluid comprises plasma.

29. The method of claim 26, wherein the biological fluid is from a warm-blooded vertebrate species.

30. The method of claim 29, wherein the warm-blooded vertebrate species is selected from the group consisting of human, canine, porcine, bovine, guinea pig, horse, cat, monkey, sheep, rat, mouse, goat, rabbit, manatee, llama, and camel.

31. The method of claim 30, wherein the biological fluid comprises plasma.

32. The method of claim 14, wherein the antibody is a polyclonal antibody.

33. The method of claim 15, wherein the antibody of step (A) is a polyclonal antibody.

34. The method of claim 15, wherein the second antibody of step (B) is a polyclonal antibody.

35. The method of claim 16, wherein the antibody of step (A) is a polyclonal antibody raised in a vertebrate species.

36. The method of claim 35, wherein the vertebrate species in which the polyclonal antibody is raised is selected from the group consisting of rabbit and goat.

37. The method of claim 16, wherein the second antibody of step (B) is a polyclonal antibody raised in a vertebrate species.

38. The method of claim 37, wherein the vertebrate species in which the polyclonal antibody is raised is selected from the group consisting of rabbit and goat.

39. The method of claim 35, wherein the sample is from a vertebrate species different from the vertebrate species in which the polyclonal antibody of step (A) is raised.

40. The method of claim 39, wherein the polyclonal antibody of step (A) is raised in rabbit and the sample is from a vertebrate species other than rabbit.

41. The method of claim 39, wherein the polyclonal antibody of step (A) is raised in goat and the sample is from a vertebrate species other than goat.

42. The method of claim 16, wherein the antibody of step (A) is a polyclonal antibody raised in a first vertebrate species and the second antibody of step (B) is a polyclonal antibody raised in a second vertebrate species different from the first vertebrate species.

43. The method of claim 42, wherein the first vertebrate species is goat and the second vertebrate species is rabbit.

44. The method of claim 42, wherein the first vertebrate species is rabbit and the second vertebrate species is goat.

45. The method of claim 14, 15 or 16, wherein the epitope is necessary for functioning of the von Willebrand factor.

46. A method of detecting dysfunctional von Willebrands factor in a subject, the dysfunction being due to a lack of or an abnormality in a functional epitope in the von Willebrand factor and the subject being a vertebrate species, which comprises:

(A) obtaining a sample of plasma containing the von Willebrand factor from the subject; and (B) detecting the von Willebrand factor antigen in the sample using the method of claim 45, wherein if no or substantially no von Willebrand factor antigen is detected, the functional epitope is lacking or abnormal and dysfunctional von Willebrands factor is detected.

47. A method of diagnosing von Willebrands disease caused by dysfunctional von Willebrands factor in a vertebrate species which comprises detecting the dysfunctional von Willebrands factor according to the method of claim 46.

48. A kit for use in qualitatively detecting von Willebrand factor antigen in a test sample from a vertebrate species which comprises: (A) an amount of an antibody of claim 1 labeled with a detectable marker; (B) one standard sample having a known vol Willebrand factor antigen concentration; and (C) a control sample substantially free of von Willebrand factor antigen.

49. A kit for use in qualitatively detecting von Willebrand factor antigen in a test sample from a vertebrate species which comprises:

(A) an amount of a first antibody of claim 1;

(B) an amount of a second antibody of claim 1 labeled with a detectable marker;
(C) one standard sample having a known von Willebrand factor antigen concentration; and
(D) a control sample substantially free of von Willebrand factor antigen.

50. A kit for use in qualitatively detecting von Willebrand factor antigen in a test sample from a vertebrate species which comprises:
(A) an amount of a first antibody of claim 1;
(B) an amount of a second antibody of claim 1; and
(C) an amount of a third antibody directed to the second antibody of step (B) and labeled with a detectable marker;
(D) one standard sample having a known von Willebrand factor antigen concentration; and
(E) a control sample substantially free of von Willebrand factor antigen.

51. A kit for use in quantitatively determining the amount of von Willebrand factor antigen in a test sample from a vertebrate species which comprises:
(A) an amount of an antibody of claim 1 labeled with a detectable marker;
(B) a series of standard samples having a known von Willebrand factor antigen concentration; and
(C) a control sample substantially free of von Willebrand factor antigen.

52. A kit for use in quantitatively determining the amount of von Willebrand factor antigen in a test sample from a vertebrate species which comprises:
(A) an amount of a first antibody of claim 1;
(B) an amount of a second antibody of claim 1 labeled with a detectable marker;
(C) a series of standard samples having a known von Willebrand factor antigen concentration; and
(D) a control sample substantially free of von Willebrand factor antigen.

53. A kit for use in quantitatively determining the amount of von Willebrand factor antigen in a test sample from a vertebrate species which comprises:
(A) an amount of a first antibody of claim 1;
(B) an amount of a second antibody of claim 1;
(C) an amount of a third antibody directed to the second antibody of step (B) and labeled with a detectable marker;
(D) a series of standard samples having a known von Willebrand factor antigen concentration; and
(E) a control sample substantially free of von Willebrand factor antigen.

54. The kit of claim 48, wherein the antibody is a polyclonal antibody raised in a vertebrate species.

55. The kit of claim 49, wherein the first antibody is a polyclonal antibody raised in a vertebrate species.

56. The kit of claim 50, wherein the first antibody is a polyclonal antibody raised in a vertebrate species.

57. The kit of claim 51, wherein the antibody is a polyclonal antibody raised in a vertebrate species.

58. The kit of claim 52, wherein the first antibody is a polyclonal antibody raised in a vertebrate species.

59. The kit of claim 53, wherein the first antibody is a polyclonal antibody raised in a vertebrate species.

60. The kit of claim 54, 55, 56, 57, 58 or 59, wherein the vertebrate species in which the polyclonal antibody is raised is selected from the group consisting of rabbit and goat.

61. The kit of claim 49, 50, 52 or 53 wherein the second antibody is a polyclonal antibody raised in a vertebrate species.

62. The kit of claim 61, wherein the vertebrate species in which the polyclonal antibody is raised is selected from the group consisting of rabbit and goat.

63. The kit of claim 50 or 53 wherein the first antibody is a polyclonal antibody raised in a goat, the second antibody is a polyclonal antibody raised in a rabbit, and the third antibody is an anti-rabbit IgG.

64. The kit of claim 50 or 53 wherein the first antibody is a polyclonal antibody raised in a rabbit, the second antibody is a polyclonal antibody raised in a goat, and the third antibody is an anti-goat IgG.

65. The kit of claim 48, 49, 50, 51, 52 or 53 wherein the detectable marker is an enzyme.

66. The kit of claim 65, wherein the enzyme is horseradish peroxidase.

67. The kit of claim 65, wherein the enzyme is alkaline phosphatase.

68. A method of quantitatively determining the amount of von Willebrand factor antigen in a test sample from a vertebrate species using the kit of claim 51 which comprises:
(A) separately contacting each of the test sample, said standard samples, and the control sample with said antibody such that any von Willebrand factor antigen in each of said samples binds to the antibody and each forms a complex therewith;
(B) separately detecting the amount of said antibody present in each of said complexes formed in step (A), thus detecting the von Willebrand factor antigen in each of said test sample, said standard samples, and said control sample; and
(C) comparing, the amount of antibody present in each of said test sample, said standard samples, and said control sample to quantitatively determine the amount of von Willebrand factor antigen in the test sample.

69. A method of quantitatively determining the amount of von Willebrand factor antigen in a test sample from a vertebrate species using the kit of claim 52 which comprises:
(A) separately contacting each of the test sample, said standard samples, and said control sample with said first antibody such that any von Willebrand factor antigen in each of said samples binds to said first antibody and each forms a complex therewith;
(B) separately contacting each of said complexes formed in step (A) with said second antibody so as to form a second complex for each which includes said first antibody, said von Willebrand factor antigen, and said second antibody;
(C) separately detecting said amount of second antibody present in each of the second complexes, formed in step (B), thus detecting said von Willebrand factor antigen in each of said test sample, said standard samples, and said control sample; and
(D) comparing the amount of second antibody present in each of said test sample, standard samples, and control sample to quantitatively determine the amount of von Willebrand factor antigen in the test sample.

70. A method of quantitatively determining the amount of von Willebrand factor antigen in a test sample from a vertebrate species using the kit of claim 53 which comprises:
(A) separately contacting each of the test sample, said standard samples, and said control sample with said first antibody such that any von Willebrand factor, antigen in each of said samples binds to said first antibody and each forms a complex therewith;

(B) separately contacting each of said complexes formed in step (A) with said second antibody so as to form a second complex for each which includes said first antibody, said von Willebrand factor antigen, and said second antibody;

(C) separately contacting each of said second complexes formed in step (B) with said third antibody so as to form a third complex for each which includes said first antibody, said von Willebrand factor antigen, said second antibody, and said third antibody;

(D) separately detecting the amount of said third antibody present in each of said third complexes formed in step (C), thus detecting the von Willebrand factor antigen in each of said test sample said standard samples, and said control sample; and (E) comparing the amount of said third antibody present in each of said test sample, said standard samples, and said control sample to quantitatively determine the amount of von Willebrand factor antigen in said test sample.

71. The method of claim 14, wherein the antibody is a monoclonal antibody.

72. The method of claim 15, wherein the antibody of step (A) is a monoclonal antibody.

73. The method of claim 15, wherein the second antibody of step (B) is a monoclonal antibody.

74. The method of claim 16, wherein the antibody of step (A) is a monoclonal antibody.

75. The method of claim 16, wherein the second antibody of step (B) is a monoclonal antibody.

76. The kit of claim 48, wherein the antibody is a monoclonal antibody.

77. The kit of claim 49, wherein the first antibody is a monoclonal antibody.

78. The kit of claim 50, wherein the first antibody is a monoclonal antibody.

79. The kit of claim 51, wherein the antibody is a monoclonal antibody.

80. The kit of claim 52, wherein the first antibody is a monoclonal antibody.

81. The kit of claim 53, wherein the first antibody is a monoclonal antibody.

82. The kit of claim 49, 50, 52 or 53 wherein the second antibody is a monoclonal antibody.

* * * * *

UNITED STATES PATENT AND TRADEMARK OFFICE
CERTIFICATE OF CORRECTION

PATENT NO. : 5,202,264
DATED : April 13, 1993
INVENTOR(S) : Roger E. Benson et al It is certified that error appears in the above-indentified patent and that said Letters Patent is hereby corrected as shown below:

On the cover page, item [63] Related U.S. Application Data, change "428, 161, Jan. 11, 1990" to --428, 161, Oct. 27, 1989--.

In column 1, line 12, change "Jan. 11, 1990" to --October 27, 1989--.

In claim 1, column 38, 21, after "being capable of" insert --recognizing an epitope of the von Willebrand--.

In claim 19, column 39, line 36, change "of claim 18" to --of claim 17--.

In claim 48, column 40, line 62, change "vol Willebrand" to --von Willebrand--.

In claim 68, column 42, line 32, change "comparing," to --comparing--.

In claim 68, column 42, line 53, change "complexes," to --complexes--.

In claim 70, column 42, line 68, change "factor," to --factor--.

In claim 70, column 43, line 2, change "therewith:" to --therewith;--.

In claim 70, column 43, line 17, change "test sample" to --test sample,--.

Signed and Sealed this

Twenty-second Day of February, 1994

Attest:

BRUCE LEHMAN

Attesting Officer

Commissioner of Patents and Trademarks